United States Patent [19]

Yamatsu et al.

[11] Patent Number: 4,888,439
[45] Date of Patent: Dec. 19, 1989

[54] POLYPRENYL COMPOUND AND PHARMACEUTICAL USE

[75] Inventors: Isao Yamatsu; Takeshi Suzuki; Shinya Abe, all of Ibaragi; Kouji Nakamoto, Tsuchiura; Akiharu Kajiwara, Ibaragi; Manabu Murakami, Ibaragi; Kiyoshi Oketani, Ibaragi; Hideaki Fujisaki, Ibaragi, all of Japan

[73] Assignee: Eisai Co., Ltd., Tokyo, Japan

[21] Appl. No.: 729,444

[22] Filed: May 1, 1985

[30] Foreign Application Priority Data

May 9, 1984 [JP] Japan .................................. 59-90995

[51] Int. Cl.$^4$ ..................... C07C 101/02; C07C 69/66
[52] U.S. Cl. ..................................... 560/129; 560/155; 560/170; 560/174; 560/183; 560/185; 560/187; 564/199
[58] Field of Search ........................ 564/199; 568/205; 560/129, 155, 187, 170, 183, 185, 174

[56] References Cited

U.S. PATENT DOCUMENTS 4,388,312  6/1983  Terao et al. .................... 260/396 R

*Primary Examiner*—Glennon H. Hollrah
*Assistant Examiner*—Raymond Covington
*Attorney, Agent, or Firm*—Flynn, Thiel, Boutell & Tanis

[57] ABSTRACT

A novel polyprenyl compound is identified with the formula and useful for a pharmaceutical drag.

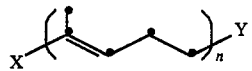

wherein X represents a group of the formula:

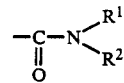

(wherein $R^1$ and $R^2$, which may be the same or different, represent each a hydrogen atom, a lower alkyl group, a hydroxyalkyl group, or a lower alkenyl group); a group of the formula:

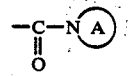

(wherein A including the nitrogen atom shown represents a ring containing nitrogen and oxygen atoms); or a group of the formula:

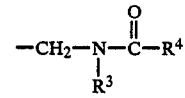

(wherein $R^3$ represents a hydrogen atom or a lower alkyl group, and $R^4$ represents a lower alkyl group); Y represents a group of the formula:

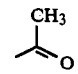

or a group of the formula:

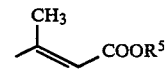

(wherein $R^5$ represents a hydrogen atom or a lower alkyl group), and n represents an integer of from 2 to 5.

8 Claims, No Drawings

POLYPRENYL COMPOUND AND PHARMACEUTICAL USE

This invention relates to a novel polyprenyl compound having an excellent medicinal effect.

More particularly, this invention relates to a polyprenyl compound represented by the general formula:

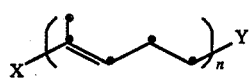 (I)

wherein X represents a group of the formula:

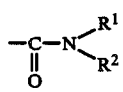

(wherein $R^1$ and $R^2$, which may be the same or different, represent each a hydrogen atom, a lower alkyl group, a hydroxyalkyl group, or a lower alkenyl group); a group of the formula:

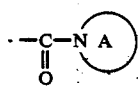

(wherein A including the N atom shown represents a ring containing nitrogen and oxygen atoms); or a group of the formula:

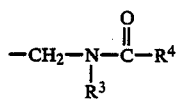

(wherein $R^3$ represents a hydrogen atom or a lower alkyl group, and $R^4$ represents a lower alkyl group); Y represents a group of the formula:

or a group of the formula:

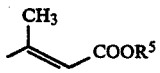

(wherein $R^5$ represents a hydrogen atom or a lower alkyl group), and n represents an integer of from 2 to 5, to a process for producing the same, and to a medicine containing the same.

In the definition of the compound (I) of this invention, the lower alkyl groups refer to linear or branched alkyl groups of 1 to 6 carbon atoms, for example, alkyl groups such as methyl, ethyl, n-propyl, isopropyl, n-butyl, isobutyl, 1-methylpropyl, tert-butyl, n-pentyl, 1-ethylpropyl, isoamyl and n-hexyl groups, and the lower alkenyl groups refer to those derived from the above-mentioned lower alkyl groups.

In the definition of a group of the formula:

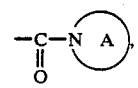

A including the N atom shown refers to a ring containing nitrogen and oxygen atoms. Typical examples of these rings have five- and six-membered rings and preferably include those represented by

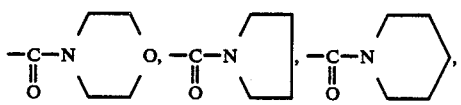

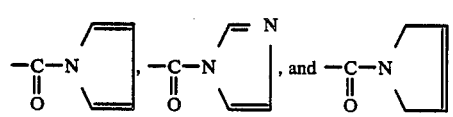

Although it is probable from its structure that the polyprenyl compound of this invention takes a variety of forms of stereoisomers (e.g., cis- and transisomers), any of these stereoisomers may be included in this invention.

The compound of this invention may be produced by a variety of methods, and typical processes among them are set forth below:

PRODUCTION PROCESS A

Cases wherein, in formula (I), X represents a group of the formula:

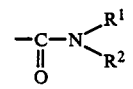

(wherein $R^1$ and $R^2$ are the same as defined above) or a group of the formula:

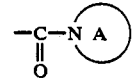

(wherein A is the same as defined above), and n is the same as defined above).

PRODUCTION PROCESS 1

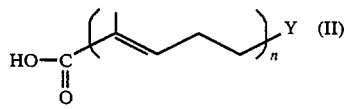 (II)

(Step 1) | acyl halide formation (SOCl$_2$, etc.)

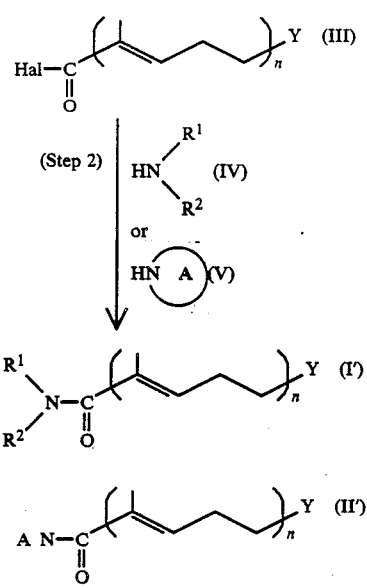

In formula (III) above, Hal, represents a halogen atom.

Namely, a polyprenylcarboxylic acid represented by formula (II) is reacted with thionyl chloride or oxalyl chloride to form an acyl halide (III), which is reacted by a usual method with a compound represented by formula (IV) or (V) to form the desired substance (I') or (II') as an amide. In each of steps 1 and 2, the reaction may be effected more smoothly when carried out in the presence of, if necessary, an organic solvent such as benzene, toluene, chloroform, isopropyl ether, nitromethane, ethyl ether, ethyl acetate, methyl ethyl ketone, tetrahydrofuran, or dioxane.

PRODUCTION PROCESS 2

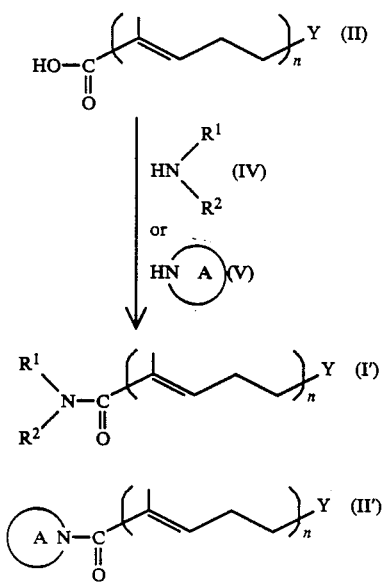

In the above formulas (II), (IV), (V), (I') and (II'), n, $R^1$, $R^2$, A, and Y are the same as defined above.

Namely, a polyprenylcarboxylic acid represented by formula (II) is reacted with a compound (IV) or (V) by using a condensing agent such as p-toluenesulfonyl chloride, ethyl chlorocarbonate, dicyclohexylcarbodiimide (DCC), diethyl chlorophosphate, or diphenylphosphoric amide optionally in the presence of an organic solvent such as benzene, toluene, chloroform, isopropyl ether, nitromethane, ethyl ether, ethyl acetate, methyl ethyl ketone, tetrahydrofuran, or dioxane to form an amide compound [(I') or (II')].

PRODUCTION PROCESS B

Cases wherein, in formula (I), X represents a group of the formula:

$$-CH_2-N(R^3)-\overset{O}{\underset{\|}{C}}-R^4$$

(wherein $R^3$ and $R^4$ are the same as defined above), and Y and n are the same as defined above,

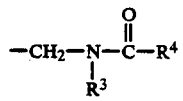

according to Production Process A | $NH_2R_3$ (VI)

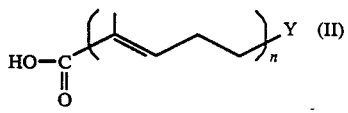

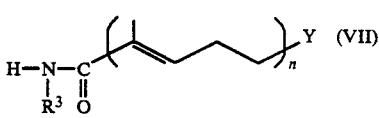

$R^4COOH$ or its reactive acid derivative (IX)

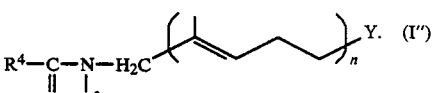

Namely, a polyprenylcarboxylic acid represented by formula (II) is aminated by reaction with a compound of formula (VI) according to, for example, the method of Production Process A to form a compound (VII), which is reduced to an amine represented by the formula (VIII). This amine is amidated with a carboxylic acid represented by formula (IX) or a reactive acid derivative such as an acyl halide according to, for example, the method of Production Process A to form the desired substance (I'').

This amidation is carried out according to the method described in Production Process A. The reduction is carried out by using, for example, lithium aluminum hydride or diborane. The solvent suitable for this case includes tetrahydrofuran and methylene chloride.

The polyprenyl compound which is provided by this invention exhibits an excellent effect of inhibiting gastric acid secretion and is useful as a drug for treating and preventing peptic ulcer.

Although there are still different views about the cause of peptic ulcer, it is essentially thought to be developed by the disturbance of a balance between ulcer-promoting factors and protective factors. Therefore, it can be generally said that medicines which can inhibit the secretion of the acid and pepsin and strengthen a mucosal protective action are ideal drugs for peptic ulcer.

At present, antagonists to histamine $H_2$ receptors which are more specific to gastric acid secretion have been spotlighted by the advent of Cimetidine, and have received international appreciation. Therefore, studies and development of medicines of this kind are being made actively in various countries.

However, the medicines of this kind have problems of a rebound phenomenon of acid secretion, recidivation, and reinflammation, and these problems have recently come to the fore. Presumably, this may result from the marked deviation from the phsiological environment of the stomach and from the regeneration of the epithelium, with the fundus of the ulcer being left unripe.

Meanwhile, anticholinergic agents have less organ-specificity in their effects so that it is difficult to differentiate their effect of inhibiting gastric acid secretion from other pharmacological effects, thus limiting the scope of application inevitably.

Although antiacids, pepsin antagonists, gastrin antagonists, and drugs for mucosa protection and anagenesis acceleration are available as drugs for peptic ulcer such as gastric or duodenal ulcer, none of these are satisfactory because of various side effects and large individual differences among patients. Therefore, it is eagerly demanded to develop an ideal, versatile drug for treating and preventing peptic ulcer.

As a result of extensive studies which have long been repeated to develop an ideal drug for peptic ulcer which inhibits secretion of acid and pepsin and strengthens mucosa protection ability, the inventors of this invention have found that a polyprenyl compound represented by the following chemical structure can satisfy this object, and achieved this invention.

Namely, this invention relates to a polyprenyl compound represented by the general formula:

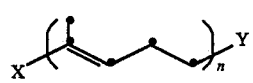

(I)

wherein X represents a group of the formula:

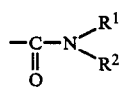

(wherein $R^1$ and $R^2$, which may be the same or different, represent each a hydrogen atom, a lower alkyl group, a hydroxyalkyl group, or a lower alkenyl group); a group of the formula:

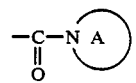

(wherein A including the N atom shown represents a ring containing nitrogen and oxygen atoms); or a group of the formula:

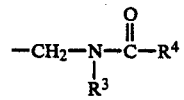

(wherein $R^3$ represents a hydrogen atom or a lower alkyl group, and $R^4$ represents a lower alkyl group); Y represents a group of the formula:

or a group of the formula:

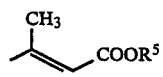

(wherein $R^5$ represents a hydrogen atom or a lower alkyl group), and n represents an integer of from 2 to 5.

Although the compound of this invention is essentially a polyprenyl compound as evident from formula (I), its feature is that it carries functional groups at both of its terminals.

The characteristics of the compound of this invention as a drug for peptic ulcer are that it can be distributed and transferred especially to the gastric tissue in high percentages; that its effect of inhibiting acid secretion is thought to be exhibited at peripheries, because no cholinergic action is observed and no indication of a central action can be seen; that it has a character concerning sugar protein synthesis; and that it has extremely high safety.

Therefore, the compound of this invention is useful as a drug for treating and preventing peptic ulcers such as gastric ulcer, and further as a drug for treating and preventing gastritis and duodenitis.

EXPERIMENTAL EXAMPLE 1

Gastric Acid Secretion Inhibiting Effect

According to the method of H. Shay et al. described in Gastroenterology, Vol. 5, p. 43 (1945), Wistar strain male rats each weighing about 200 g were not given any diet for 24 hours, and their pyloric segments were ligated under etherization. After four hours, the stomachs were excited under deep etherization, and the contents of the stomachs were collected. After determination of the amount, the gastric juice was centrifuged at 3,000 rpm for 10 minutes and the supernatant liquid was tritrated by neutralization (at a pH 7.0) with N/50-NaOH by means of an automatic titrator (TTA 81, Radiometer, Copenhagen) to determine the acidity. The amount of the acid which had been secreted for four hours was calculated from the volume of the gastric juice and the acidity. The results are represented in terms of % inhibition with respect to the control group.

Each of the compounds tested was emulsified in a 25% decaglyn mixture (polyglycerin fatty acid ester), and 100 mg/μg (dose 0.2 ml/100 g weight) was administered to the duodenum during the ligation of the pyloric segment. In the control group, only the solvent was administered. The results are shown in Table 1.

Test compounds

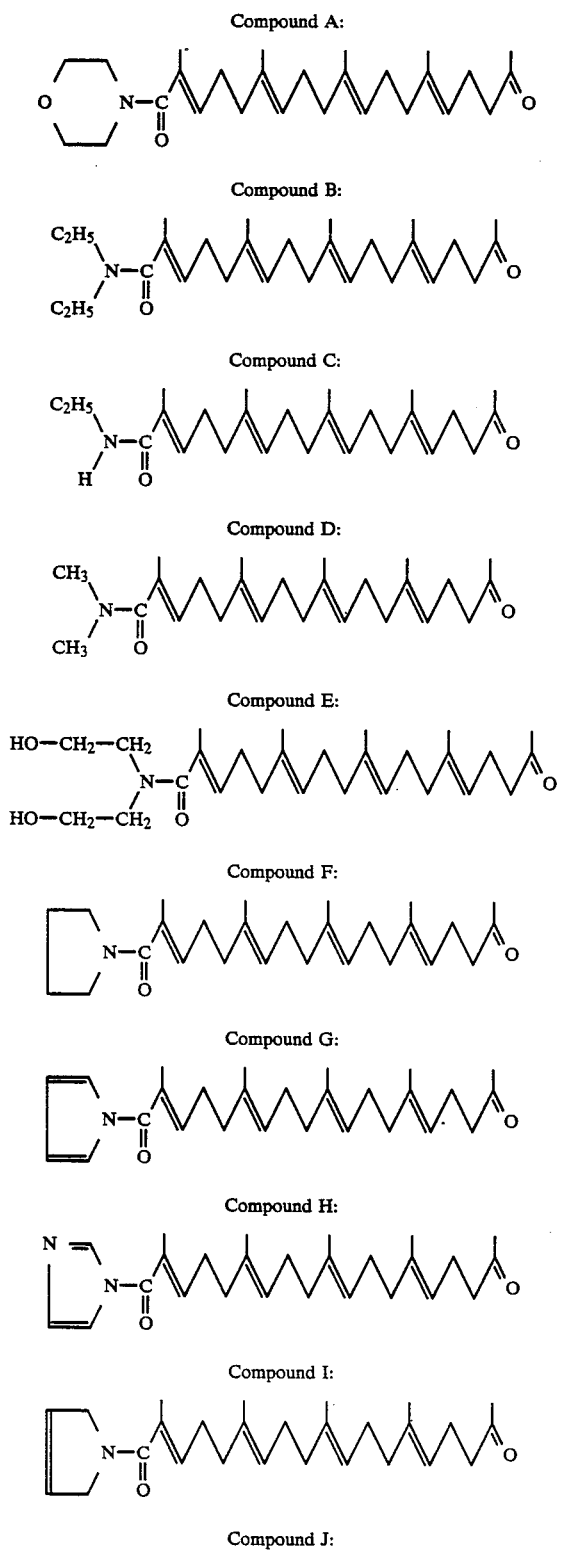

Compound K:

Compound L:

Compound M:

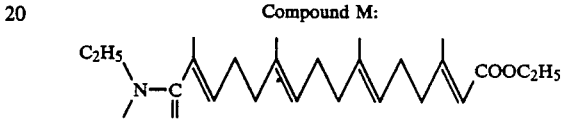

TABLE 1

| Compound | Inhibition of gastric acid secretion (%) |
|---|---|
| Compound A | 52.9 |
| Compound B | 83.5 |
| Compound C | 63.2 |
| Compound D | 52.6 |
| Compound E | 52.2 |
| Compound F | 76.1 |
| Compound G | 68.3 |
| Compound H | 49.1 |
| Compound I | 43.9 |
| Compound J | 53.0 |
| Compound K | 50.2 |
| Compould L | 62.6 |
| Compound M | 80.6 |

EXPERIMENTAL EXAMPLE 2

Effect on Experimental Ulcer

1. Effect on pyloric ligation ulcer

According to the method of Shay et al. described in Gastroenterology, Vol 5, p. 43 (1945), Wistar strain male rats each weighing about 300 g were not given any diet for 48 hours, and then their pyloric segments were ligated. After 15 hours, the abdomen of each of the rats were opened, and the stomach was excised. The stomach was cut open along the side of the greater curvature, and the ulcers developed on the fore-stomach were classified and evaluated with the naked eye into five stages. The larger ulcer index means the more ulcers and index V refers to an example of perforation. The medicines were evaluated by determining their mean±standard error. Compound B which had a powerful action of inhibiting acid secretion in Test 1, i.e. N-(2,6,10,14-tetramethyl-18-oxo-2,6,10,14-nonadecatetraenyol)-diethylamine, was selected as the test medicine and emulsified in a 2.5% decaglyn mixture, and 25 to 200 mg/kg (dose volume 0.2 ml/100 g. weight) was administered to the duodenum during the ligation of the pylorus. Cimetidine and propantheline were selected as control medicines.

The results are shown in Table 2.

TABLE 2

| Test Compound | Dose (mg/kg) | N | \multicolumn{6}{c}{Grade Index} | G.I. mean ± S.E. |
|---|---|---|---|---|---|---|---|---|---|
| | | | 0 | I | II | III | IV | V | |
| Control | — | 10 | 1 | 0 | 2 | 1 | 1 | 5 | 3.6 ± 0.6 |
| Compound B | 25 | 6 | 2 | 1 | 2 | 0 | 0 | 1 | 1.7 ± 0.7 |
| Compound B | 50 | 6 | 2 | 3 | 0 | 0 | 0 | 1 | 1.3 ± 0.8 |
| Compound B | 100 | 4 | 4 | 0 | 0 | 0 | 0 | 0 | 0.0 ± 0.0 |
| Compound B | 200 | 4 | 4 | 0 | 0 | 0 | 0 | 0 | 0.0 ± 0.0 |
| Cimetidine | 100 | 10 | 2 | 0 | 1 | 2 | 0 | 5 | 3.3 ± 0.7 |
| Propantheline bromide | 30 | 10 | 8 | 2 | 0 | 0 | 0 | 0 | 0.2 ± 0.1 |

(Note)
In Table 2, Grade Index was evaluated on the basis of the size, number, and severity of ulcers.

2. Effect on ethanol-induced ulcer

According to the method of Robert et al., 1 ml/rat of absolute ethanol was administered orally to each of Wistar male rats. After one hour, the stomach of each rat was excised, 10 ml of physiologically saline solution was injected into the stomach, and the stomach was soaked in 5% neutral formalin. Each stomach was cut open along the side of the greater curvature, and the ulcers developed on the glandular stomach were measured for their lengths and the total sum of the lengths was defined as ulcer index.

Compound B, i.e. N-(2,6,10,14-tetramethyl-18-oxo-2,6,10,14-nonadecatetraenoyl)diethylamine, and compound F, i.e. N-(2,6,10,14-tetramethyl-18-oxo-2,6,10,14-nonadecatetraenoyl)pyrrolidine, were selected as test compounds and emulsified in 2.5% decaglyn mixture, and 12.5 to 100 mg/kg (dose volume 0.2 ml/100 g-weight) was administered orally 30 minutes before administration of ethanol.

The results are shown in Table 3.

TABLE 3

| Compound Test | Dose (mg/kg) | N | Ulcer Index Mean ± S.E. (mm) | Inhibition (%) |
|---|---|---|---|---|
| Control | — | 6 | 58.1 ± 8.9 | — |
| Compound B | 12.5 | 4 | 10.1 ± 5.9*** | 82.6 |
| Compound B | 25 | 5 | 1.4 ± 1.0*** | 97.6 |
| Compound B | 50 | 6 | 5.6 ± 2.9*** | 90.4 |
| Compound B | 100 | 6 | 1.3 ± 1.0*** | 97.8 |
| Compound F | 12.5 | 5 | 21.4 ± 8.2** | 63.2 |
| Compound F | 25 | 6 | 3.0 ± 1.9*** | 94.8 |
| Compound F | 50 | 6 | 8.3 ± 3.4*** | 85.7 |
| Compound F | 100 | 6 | 1.7 ± 0.9** | 97.1 |

(Note)
In Table 3, data with a mark  are significant at $p < 0.01$, and those with a mark * are significant at $p < 0.001$.

The results of the above pharmacological experiments clearly show that the compounds of this invention have an excellent effect of inhibiting acid secretion.

The compound of this invention is useful as a drug for treating and preventing peptic ulcer such as gastric or duodenal ulcer and as a drug for treating and preventing gastritis or duodenitis as well. Because of the natures of these diseases, this compound must be administered continuously for a long time, but the compound of this invention shows extremely low toxicity and high safety so that it is valuable in this sense. Its toxicity ($LD_{50}$) is such that the $LD_{50}$ (mouse, orally) is above 5,000 mg/kg for compounds D and F.

Though the dose of the compound of this invention which is given to patients of the above-mentioned diseases is not particularly limited and varies with the kind of a disease, the severity of condition, the kind of a compound, the age of a patient, etc., it is administered orally or parenterally in a dose of 50 to 2,000 mg, preferably 50 to 300 mg per adult-day. The compound is administered preferably in divided portions (2 to 4 times a day). The dose forms include, for example, powder, fine granules, granules, capsules, and injections. The drugs are prepared from the compounds by using a usual carrier in a conventional method.

Namely, an oral solid preparation is produced by mixing a basis with an excipient and, optionally, a binder, a disintegrator, a lubricant, a colorant, and a corrigent, and forming the mixture into tablets, coated tablets, granules, powder, capsules, etc., by a usual method.

The excipients include, for example, lactose, cornstarch, white sugar, dextrose, sorbitol, crystalline cellulose, and silicon dioxide. The binders include, for example, polyvinyl alcohol, polyvinyl ether, ethylcellulose, methylcellulose, gum arabic, tragacanth, gelatin, shellac, hydroxypropylcellulose, hydroxypropylstarch, and polyvinylpyrrolidone. The disintegrators include, for example, starch, agar-agar, gelatin powder, crystalline cellulose, calcium carbonate, sodium hydrogencarbonate, calcium citrate, and pectin. The lubricants include, for example, magnesium stearate, talc, polyethylene glycol, silica, and hardened vegetable oils. The colorants include compounds which are acceptable as additives to drugs. The corrigent include cocoa powder, methanol, aromatic powder, peppermint oil, borneol, and cinnamon powder. It is of course possible to apply sugar, gelatin, or other suitable coatings to these tablets or granules.

An injection is prepared by mixing a basis with, optionally, a pH controlling agent, a buffer agent, a stabilizer, a solubilizer, etc., and forming the mixture by a usual method into a hypodermic, intramuscular or intraveneous injection.

Now the description will be given of an example of a preparation containing, as an effective ingredient, N-(2,6,10,14-tetramethyl-18-oxo-2,6,10,14-nonadecatetraenoyl)pyrrolidine (Example 9) (hereinafter referred to as a basis) which is a typical compound of the compounds of this invention.

| Preparation example (tablets) | |
|---|---|
| basis | 10 g |
| silicic anhydride | 50 g |
| crystalline cellulose | 70 g |
| cornstarch | 36 g |
| hydroxypropylcellulose | 10 g |
| magnesium stearate | 4 g |

According to the above recipe, tablets (each weighing 180 mg) were formed by a usual method.

Part of the examples of this invention will now be described, but it should be noted that this invention is by no means limited thereto.

EXAMPLE 1

N-(2,6,10,14-tetramethyl-18-oxo-2,6,10,14-nonadecatetraenoyl)dimethylamine

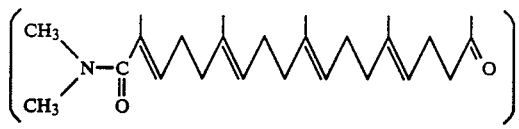

(Production process 1)

5 g of 2,6,10,14-tetramethyl-18-oxo-2,6,10,14-nonadecatetraenoic acid was dissolved in 30 ml of benzene, 3.3 g of thionyl chloride was added thereto, and the mixture was heated under reflux for 30 minutes. The resulting solution was concentrated in vacuum and dissolved in 30 ml of benzene. The obtained solution was added dropwise to 10 ml of a 50% aqueous dimethylamine solution under cooling with ice. The resulting solution was agitated as such for 30 minutes, washed with dilute hydrochloric acid and then with water, and concentrated. The residue was purified by means of silica gel column chromatography to obtain 4.9 g (yield: 91%) of the title compound.

Elementary analysis: as $C_{25}H_{41}O_2N$.

|  | C | H | N |
|---|---|---|---|
| Calculated (%) | 77.47 | 10.67 | 3.61 |
| Found (%) | 77.51 | 10.59 | 3.58 |

Mass (m/z): 387M+.

$^1$H-NMR (CDCl$_3$) δ: 1.59 (9H, s), 1.82 (3H, s), 1.9–2.5 (14H), 2.12 (3H, s), 2.28 (2H, t, J=3), 2.96 (6H, s), 4.9–5.2 (3H), 5.4–5.6 (1H).

(Production Process 2)

5 g of 2,6,10,14-tetramethyl-18-oxo-2,6,10,14-nonadecatetraenoic acid was dissolved in a mixture of 30 ml of tetrahydrofuran and 5 ml of triethylamine, to which was added 2.9 g of diethyl chlorophosphate and the mixture was agitated for 30 minutes. The mixture was added dropwise to 5 ml of a 50% aqueous dimethylamine solution and the resulting mixture was agitated further for 30 minutes. The reaction mixture was poured into dilute hydrochloric acid and extracted with benzene. After washing with water, the organic layer was concentrated, and the residue was purified by means of silica gel column chromatography to obtain 4.6 g (yield: 86%) of the title compound.

EXAMPLE 2

N-(2,6,10,14-tetramethyl-18-oxo-2,6,10,14-nonadecatetraenoyl)diethylamine

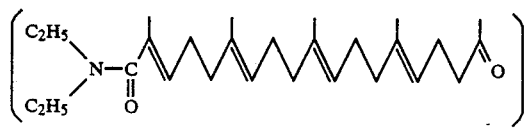

(Production Process 1)

5 g of 2,6,10,14-tetramethyl-18-oxo-2,6,10,14-nonadecatetraenoic acid was dissolved in 30 ml of benzene, 3.3 g of thionyl chloride was added thereto and the mixture was heated under reflux for 30 minutes. After vacuum concentration, the concentrate was dissolved in 30 ml of benzene, to which was added 5 ml of diethylamine under cooling with ice, and the resulting solution was agitated for 30 minutes.

The reaction solution was washed with dilute hydrochloric acid and then with water, and concentrated. The residue was purified by means of silica gel column chromatography to obtain 5 g (yield: 87%) of the title compound.

Elementary analysis: as $C_{27}H_{45}O_2N$.

|  | C | H | N |
|---|---|---|---|
| Calculated (%) | 78.02 | 10.91 | 3.37 |
| Found (%) | 78.18 | 10.78 | 3.39 |

Mass (m/z): 415M+.

$^1$H-NMR (CDCl$_3$) δ: 1.12 (6H, t, J=4), 1.60 (9H, s), 1.81 (3H, s), 1.9–2.5 (14H), 2.28 (2H, t, J=3), 3.34 (4H, q, J=4), 4.9–5.2 (3H), 5.3–5.5 (1H).

(Production Process 2)

5 g of 2,6,10,14-tetramethyl-18-oxo-2,6,10,14-nonadecatetraenoic acid was dissolved in a mixture of 30 ml of tetrahydrofuran and 5 ml of triethylamine, to which was added 2.9 g of diethyl chlorophosphate, and the mixture was agitated for 30 minutes. After adding 0.8 g of diethylamine, the mixture was further agitated for 30 minutes.

The reaction solution was poured into dilute hydrochloric acid and extracted with benzene.

The organic layer was washed and concentrated. The residue was purified by means of silica gel column chromatography to obtain 5.2 g (yield: 90%) of the title compound.

EXAMPLE 3

N-(2,6,10,14-tetramethyl-18-oxo-2,6,10,14-nonadecatetraenoyl)-n-dipropylamine

5 g of 2,6,10,14-tetramethyl-18-ox-2,6,10,14-nonadecatetraenoic acid was dissolved in 30 ml of benzene, 3.3 g of thionyl chloride was added thereto and the mixture was heated under reflux for 30 minutes. The resulting mixture was concentrated in vacuum and dissolved in 30 ml of benzene. 5 ml of dipropylamine was added dropwise thereto under cooling with ice. The resulting mixture was agitated as such for 30 minutes.

The reaction solution was washed with dilute hydrochloric acid and then with water, and concentrated. The residue was purified by means of silica gel column chromatography to obtain 5.5 g (yield: 89%) of the title compound.

Elementary analysis: as $C_{29}H_{49}O_2N$.

|  | C | H | N |
|---|---|---|---|
| Calculated (%) | 78.50 | 11.13 | 3.16 |
| Found (%) | 78.68 | 11.07 | 3.19 |

Mass (m/z): 443M+.

$^1$H-NMR (CDCl$_3$) δ: 0.86 (6H, t, J=4), 1.60 (9H, s), 1.81 (3H, s), 1.1–2.5 (18H), 2.12 (3H, s), 2.28 (2H, t, J=3), 3.1–3.3 (4H), 4.9–5.2 (3H), 5.3–5.5 (1H).

EXAMPLE 4

N-(2,6,10,14-tetramethyl-18-oxo-2,6,10,14-nonadecatetraenoyl)diisopropylamine

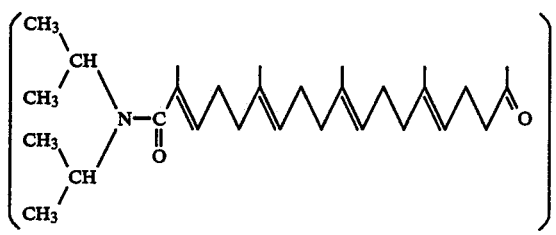

5 g of 2,6,10,14-tetramethyl-18-oxo-2,6,10,14-nonadecatetraenoic acid was dissolved in 30 ml of benzene. 3.3 g of thionyl chloride was added thereto and agitated for 30 minutes. The resulting solution was concentrated in vacuum and dissolved in 30 ml of benzene. 5 ml of diisopropylamine was added dropwise thereto, and the mixture was agitated as such for 30 minutes.

The reaction solution was washed with dilute hydrochloric acid and then with water, and concentrated. The residue was purified by means of silica gel column chromatography to obtain 5.7 g (yield: 92%) of the title compound.

Elementary analysis: as C$_{29}$H$_{49}$O$_2$N.

|  | C | H | N |
|---|---|---|---|
| Calculated (%) | 78.50 | 11.13 | 3.16 |
| Found (%) | 78.71 | 11.09 | 3.20 |

Mass (m/z): 443M+.

$^1$H-NMR (CDCl$_3$) δ: 1.29 (12H, d, J=4), 1.60 (9H, s), 1.80 (3H, s), 1.9–2.5 (14H), 2.12 (3H, s), 2.28 (2H, t, J=3), 3.5–3.8 (2H), 4.9–5.2 (3H), 5.2–5.4 (1H).

EXAMPLE 5

N-(2,6,10,14-tetramethyl-18-oxo-2,6,10,14-nonadecatetraenoyl)-n-dibutylamine

5 g of 2,6,10,14-tetramethyl-18-oxo-2,6,10,14-nonadecatetraenoic acid was dissolved in 30 ml of benzene. 3.3 g of thionyl chloride was added thereto, and the mixture was heated under reflux for 30 minutes. The obtained solution was concentrated in vacuum and dissolved in 30 ml of benzene. 5 ml of n-dibutylamine was added dropwise thereto under cooling with ice, and the mixture was agitated as such for 30 minutes.

The reaction solution was washed with dilute hydrochloric acid and then with water, and concentrated. The residue was purified by means of silica gel column chromatography to obtain 5.4 g (yield: 83%) of the title compound.

Elementary analysis: as C$_{31}$H$_{53}$O$_2$N.

|  | C | H | N |
|---|---|---|---|
| Calculated (%) | 78.92 | 11.32 | 2.97 |
| Found (%) | 78.98 | 11.30 | 2.98 |

Mass (m/z): 471M+.

$^1$H-NMR (CDCl$_3$) δ: 0.86 (6H, t, J=4), 1.86 (3H, s), 1.1–2.5 (22H), 2.12 (3H, s), 2.29 (2H, t, J=3), 3.1–3.3 (4H), 4.9–5.2 (3H), 4.9–5.2 (3H), 5.3–5.5 (1H)

EXAMPLE 6

N-(2,6,10,14-tetramethyl-18-oxo-2,6,10,14-nonadecatetraenoyl)diisobutylamine

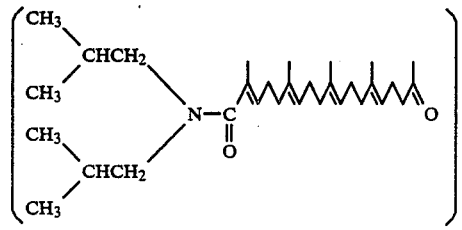

5 g of 2,6,10,14-tetramethyl-18-oxo-2,6,10,14-nonadecatetraenoic acid was dissolved in 30 ml of benzene. 3.3 g of thionyl chloride was added thereto and the mixture was heated under reflux for 30 minutes. The resulting solution was concentrated in vacuum and dissolved in 30 ml of benzene. 5 ml of diisobutylamine was added dropwise thereto under cooling with ice. The mixture was agitated as such for 30 minutes.

The reaction solution was washed with dilute hydrochloric acid and then with water, and concentrated. The residue was purified by means of silica gel column chromatography to obtain 5.8 g (yield: 89%) of the title compound.

Elementary analysis: as C$_{31}$H$_{53}$O$_2$N.

|  | C | H | N |
|---|---|---|---|
| Calculated (%) | 78.92 | 11.32 | 2.97 |
| Found (%) | 79.03 | 11.18 | 3.02 |

Mass (m/z): 471M+.

$^1$H-NMR (CDCl$_3$) δ: 0.84 (12H, d, J=4), 1.60 (9H, s), 1.79 (3H, s), 1.1–2.5 (18H), 2.12 (3H, s), 3.17 (4H, d, J=6), 4.9–5.2 (3H), 5.3–5.6 (1H).

EXAMPLE 7

2,6,10,14-tetramethyl-18-oxo-2,6,10,14-nonadecatetraenamide

5 g of 2,6,10,14-tetramethyl-18-oxo-2,6,10,14-nonadecatetraenoic acid was dissolved in 30 ml of benzene. 3.3 g of thionyl chloride was added thereto and the mixture was heated under reflux for 30 minutes. The resulting solution was concentrated in vacuum and dissolved in 30 ml of benzene. The solution was added dropwise under cooling with ice to 30 ml of 28% ammonia water. The resulting mixture was agitated as such for 30 minutes.

The reaction solution was washed with dilute hydrochloric acid and then with water, and concentrated. The residue was purified by means of silica gel column chromatography to obtain 4.1 g (yield: 82%) of the title compound.

Elementary analysis: as $C_{23}H_{37}O_2N$.

|  | C | H | N |
|---|---|---|---|
| Calculated (%) | 76.83 | 10.37 | 3.90 |
| Found (%) | 76.97 | 10.32 | 3.97 |

Mass (m/z): 359M+.
$^1$H-NMR (CDCl$_3$) δ: 1.60 (9H, s), 1.84 (3H, s), 1.90–2.5 (14H), 2.13 (3H, s), 2.32 (2H, t, J=3), 4.9–5.2 (3H), 5.5–5.8 (1H), 6.2–6.5 (2H).

EXAMPLES 8 THROUGH 13

The following compounds were obtained by using the compounds set forth below as starting materials in the same way as in Example 7.

EXAMPLE 8

N-(2,6,10,14-tetramethyl-18-oxo-2,6,10,14-nonadecatetraenoyl)ethylamine

Starting materials: 2,6,10,14-tetramethyl-18-oxo-2,6,10,14-nonadecatetraenoic acid and a 70% aqueous ethylamine solution Elementary analysis: as $C_{25}H_{41}O_2N$.

|  | C | H | N |
|---|---|---|---|
| Calculated (%) | 77.47 | 10.67 | 3.61 |
| Found (%) | 77.61 | 10.59 | 3.60 |

Mass (m/z): 387M+.
$^1$H-NMR (CDCl$_3$) δ: 1.16 (3H, t, J=4), 1.60 (9H, s), 1.83 (3H, s), 1.9–2.6 (14H), 2.11 (3H, s), 2.27 (2H, t, J=3), 3.1–3.5 (2H), 4.9–5.2 (3H), 5.5–5.8 (1H), 6.1–6.3 (1H).

EXAMPLE 9

N-(2,6,10,14-tetramethyl-18-oxo-2,6,10,14-nonadecatetraenoyl)pyrrolidine

Starting materials: 2,6,10,14-tetramethyl-18-oxo-2,6,10,14-nonadecatetraenoic acid and pyrrolidine.
Elementary analysis: as $C_{27}H_{43}O_2N$.

|  | C | H | N |
|---|---|---|---|
| Calculated (%) | 78.40 | 10.48 | 3.39 |
| Found (%) | 78.57 | 10.38 | 3.44 |

Mass (m/z): 413M+.
$^1$H-NMR (CDCl$_3$) δ: 1.59 (9H, s), 1.83 (3H, s), 1.9–2.4 (18H), 2.11 (3H, s), 2.28 (2H, t, J=3), 3.3–3.6 (4H), 4.9–5.2 (3H), 5.5–5.7 (1H).

EXAMPLE 10

N-(2,6,10,14-tetramethyl-18-oxo-2,6,10,14-nonadecatetraenoyl)piperidine

Starting materials: 2,6,10,14-tetramethyl-18-oxo-2,6,10,14-nonadecatetraenoic acid and piperidine.
Elementary analysis: as $C_{28}H_{45}O_2N$.

|  | C | H | N |
|---|---|---|---|
| Calculated (%) | 78.63 | 10.61 | 3.28 |
| Found (%) | 78.87 | 10.70 | 3.20 |

Mass (m/z): 427M+.
$^1$H-NMR (CDCl$_3$) δ: 1.58 (9H, s), 1.81 (3H, s), 1.9–2.5 (20H), 2.11 (3H, s), 2.29 (2H, t, J=3), 3.3–3.6 (4H), 4.9–5.2 (3H), 5.3–5.6 (1H).

EXAMPLE 11

1-(2′,6′,10′,14′-tetramethyl-18′-oxo-2′,6′,10′,14′-nonadecatetraenoyl)-3-pyrroline Starting materials: 2,6,10,14-tetramethyl-18-oxo-2,6,10,14-nonadecatetraenoic acid and 3-pyrroline.
Elementary analysis: as $C_{27}H_{41}O_2N$.

|  | C | H | N |
|---|---|---|---|
| Calculated (%) | 78.78 | 10.04 | 3.40 |
| Found (%) | 78.95 | 10.00 | 3.43 |

Mass (m/z): 411M+.
$^1$H-NMR (CDCl$_3$) δ: 1.59 (9H, s), 1.85 (3H, s), 1.9–2.6 (14H), 2.12 (3H, s), 2.29 (2H, t, J=3), 4.1–4.3 (4H), 4.9–5.2 (3H), 5.5–5.9 (2H), 6.29 (1H, t, J=1)

EXAMPLE 12

1-(2′,6′,10′,14′-tetramethyl-18′-oxo-2′,6′,10′,14′-nonadecatetraenoyl)imidazole

Starting materials: 2,6,10,14-tetramethyl-18-2,6,10,14-nonadecatetraenoic acid and imidazole (imidazole/pyridine solution).

Elementary analysis: $C_{26}H_{38}O_2N$.

|  | C | H | N |
|---|---|---|---|
| Calculated (%) | 76.05 | 9.33 | 6.82 |
| Found (%) | 76.21 | 9.20 | 6.91 |

Mass (m/z): 410M+.

$^1$H-NMR (CDCl$_3$) δ: 1.58 (9H, s), 1.82 (3H, s), 2.11 (3H, s), 1.9–2.5 (16H), 4.9–5.2 (3H), 6.9–7.0 (1H), 7.0–7.1 (1H), 7.5–7.7 (1H), 8.29 (1H, s).

EXAMPLE 13

N-(2,6,10,14-tetramethyl-18-oxo-2,6,10,14-nonadecatetraenoyl)morpholine

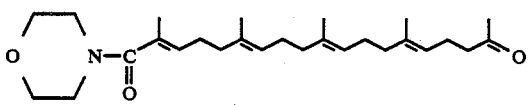

Starting materials: 2,6,10,14-tetramethyl-18-oxo-2,6,10,14-nonadeatetraenoic acid and morpholine.

Elementary analysis: as $C_{27}H_{43}O_3N$.

|  | C | H | N |
|---|---|---|---|
| Calculated (%) | 75.48 | 10.09 | 3.26 |
| Found (%) | 75.63 | 10.11 | 3.38 |

Mass (m/z): 429M+.

$^1$H-NMR (CDCl$_3$) δ: 1.6 (9H, s), 1.82 (3H, s), 1.9–2.5 (16H), 2.12 (3H, s), 3.3–3.8 (8H), 4.9–5.2 (3H), 5.3–5.6 (1H).

EXAMPLE 14

N-(2,6,10,14-tetramethyl-18-oxo-2,6,10,14-nonadecatetraenyl)

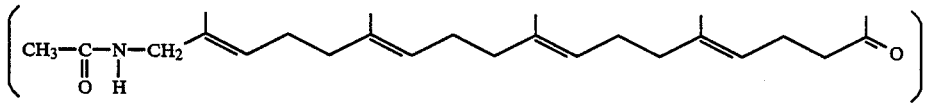

(1) 5 g of 2,6,10,14-tetramethyl-18-oxo-2,6,10,14-nonadecatetraenoic acid was dissolved in 30 ml of benzene. 3.3 g of thionyl chloride was added thereto and the mixture was heated under reflux for 30 minutes. The resulting solution was concentrated in vacuum and dissolved in 30 ml of benzene. The solution was added dropwise as such to 30 ml of ammonia water under cooling with ice, and the mixture was agitated as such for 30 minutes.

(2) The reaction solution was washed with dilute hydrochloric acid and then with water, and concentrated. The residue was dissolved in 100 ml of benzene, and 8.6 g of ethylene glycol and 0.3 g of p-toluenesulfonic acid were added thereto. The mixture was heated for 5 hours under reflux by using an azeotropic dehydration tube. The reaction solution was washed with an aqueous sodium bicarbonate solution and then with water, and concentrated. The residue was dissolved in 20 ml of tetrahydrofuran, and 5 ml of a toluene solution of (2-methoxyethoxy)-aluminum sodium was added thereto under cooling with ice. The mixture was agitated for 30 minutes. An aqueous caustic soda solution was added to the reaction solution, and the product was extracted therefrom with the ether, washed with water, and concentrated.

The residue was dissolved in ethanol. Dilute hydrochloric acid was added thereto and the mixture was allowed to stand at 50° C. for 2 hours and concentrated in vacuum. The residue was dissolved in 5 ml of pyridine, 5 ml of acetic anhydride was added thereto and the solution was allowed to stand for 2 hours.

The reaction solution was poured into dilute hydrochloric acid and extracted with benzene. The organic layer was washed with water and concentrated. The residue was purified by means of silica gel column chromatography to obtain 1.8 g (yield: 34%) of the title compound.

Elementary analysis: as $C_{25}H_{41}O_2N$.

|  | C | H | N |
|---|---|---|---|
| Calculated (%) | 77.47 | 10.67 | 3.61 |
| Found (%) | 77.68 | 10.51 | 3.73 |

Mass (m/z): 387M+.

$^1$H-NMR (CDCl$_3$) δ: 1.59 (12H, s), 2.00 (3H, s), 1.9–2.5 (16H), 2.11 (3H, s), 2.7–2.9 (2H), 4.9–5.3 (4H), 6.1–7.1 (1H).

EXAMPLES 15 THROUGH 17

The following compounds were obtained in the same way as described in Example 14. The starting materials uses in (1) were 2,6,10,14-tetramethyl-18-oxo-2,6,10,14-nonadecatetraenoic acid and the following compounds instead of ammonia, and those used in (2) were the following compounds instead of acetic anhydride.

EXAMPLE 15

N-(2,6,10,14-tetramethyl-18-oxo-2,6,10,14-nonadecatetraenyl)propionamide

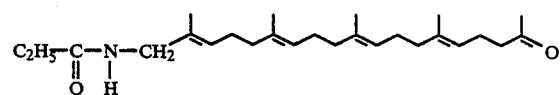

Starting materials:
(1) 2,6,10,14-tetramethyl-18-oxo-2,6,10,14-nonadecatetranoic acid and ammonia water.
(2) propionyl chloride.

Elementary analysis: as $C_{26}H_{43}O_2N$.

|  | C | H | N |
|---|---|---|---|
| Calculated (%) | 77.75 | 10.79 | 3.49 |
| Found (%) | 77.92 | 10.62 | 3.63 |

Mass (m/z): 401M+.

$^1$H-NMR (CDCl$_3$) δ: 1.16 (3H, t, J=4), 1.60 (12H, s), 1.9–2.6 (16H), 2.11 (3H, s), 2.7–2.9 (2H), 3.1–3.6 (2H), 4.9–5.3 (4H), 6.1–7.1 (1H)

EXAMPLE 16

N-ethyl-N-(2,6,10,14-tetramethyl-18-oxo-2,6,10,14-nonadecatetraenyl)acetamide

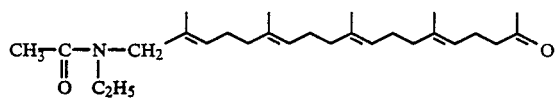

Starting materials:
(1) 2,6,10,14-tetramethyl-18-oxo-2,6,10,14-nonadecatetraenoic acid and aqueous ethylamine solution.
(2) acetic anhydride.
Elementary analysis: as $C_{27}H_{45}O_2N$.

|  | C | H | N |
|---|---|---|---|
| Calculated (%) | 78.02 | 10.91 | 3.37 |
| Found (%) | 78.17 | 10.83 | 3.28 |

Mass (m/z): 415$M^+$.
$^1$H-NMR (CDCl$_3$) δ: 1.0–1.4 (3H), 1.60 (12H, s), 1.9–2.5 (16H), 2.01 (3H, s), 2.11 (3H, s), 2.7–2.9 (2H), 3.1–3.6 (2H), 4.9–5.3 (4H).

EXAMPLE 17

N-ethyl-N-(2,6,10,14-tetramethyl-18-oxo-2,6,10,14-nonadecatetraenyl)propionamide

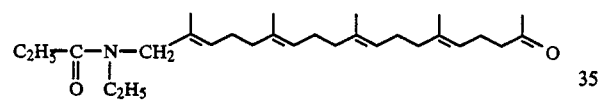

Starting materials:
(1) 2,6,10,14-tetramethyl-18-oxo-2,6,10,14-nonadecatetraenoic acid and aqueous ethylamine solution.
(2) propionyl chloride.
Elementary analysis: as $C_{28}H_{47}O_2N$.

|  | C | H | N |
|---|---|---|---|
| Calculated (%) | 78.27 | 11.03 | 3.26 |
| Found (%) | 78.45 | 10.88 | 3.33 |

Mass (m/z): 429$M^+$.
$^1$H-NMR (CDCl$_3$) δ: 1.0–1.4 (6H), 1.60 (12H, s), 2.12 (3H, s), 1.9–2.5 (16H), 2.7–2.9 (2H), 3.1–3.6 (4H), 4.9–5.3 (4H).

EXAMPLE 18

N-(2,6,10,14-trimethyl-14-oxo-2,6,10,14-pentadecatrienoyl)dimethylamine

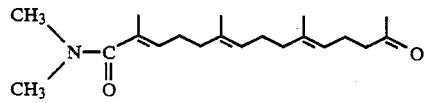

5 g of 2,6,10-trimethyl-14-oxo-2,6,10,14-pentadecatrienoic acid was dissolved in 30 ml of benzene 4.1 g of thionyl chloride was added thereto and the mixture was heated under reflux for 30 minutes. The resulting solution was concentrated in vacuum and dissolved in 30 ml of benzene. The solution was added dropwise under cooling with ice to 10 ml of a 50% aqueous dimethylamine solution, and the mixture was agitated as such for 30 minutes. The reaction solution was washed with dilute hydrochloric acid and then with water, and concentrated. The residue was purified by means of silica gel column chromatography to obtain 5.0 g (yield: 92%) of the title compound.
Elementary analysis: as $C_{20}H_{33}O_2N$.

|  | C | H | N |
|---|---|---|---|
| Calculated (%) | 75.19 | 10.41 | 4.38 |
| Found (%) | 75.30 | 10.34 | 4.40 |

Mass (m/z): 319$M^+$.
$^1$H-NMR (CDCl$_3$) δ: 1.60 (6H, s), 1.82 (3H, s), 1.9–2.5 (10H), 2.11 (3H, s), 2.29 (2H, t, J=3), 2.96 (6H, s), 4.9–5.2 (2H), 5.4–5.6 (1H).

EXAMPLES 19 THROUGH 30

The following compounds were obtained in the same way as in Example 18. Although the starting materials used in Example 18 were 2,6,10-trimethyl-14-oxo-2,6,10-pentadecatrienoic acid and an aqueous dimethylamine solution, the following starting materials were used in place of them for the synthesis.

EXAMPLE 19

N-(2,6,10-trimethyl-14-oxo-2,6,10-pentadecatrienoyl)-diethylamine

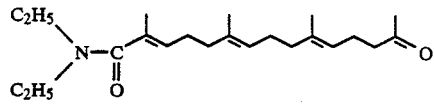

Starting materials: 2,6,10-trimethyl-14-oxo-2,6,10-pentadecatrienoic acid and diethylamine.
Elementary analysis: as $C_{22}H_{37}O_2N$.

|  | C | H | N |
|---|---|---|---|
| Calculated (%) | 76.03 | 10.73 | 4.03 |
| Found (%) | 76.27 | 10.65 | 4.11 |

Mass (m/z): 347$M^+$.
$^1$H-NMR (CDCl$_3$) δ: 1.11 (6H, t, J=4), 1.59 (6H, s), 1.82 (3H, s), 1.9–2.5 (10H), 2.11 (3H, s), 2.28 (2H, t, J=3).

EXAMPLE 20

N-(2,6,10-trimethyl-14-oxo-2,6,10-pentadecatrienoyl)-n-dipropylamine

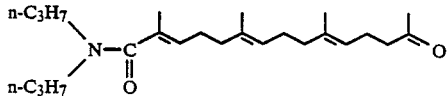

Starting materials: 2,6,10-trimethyl-14-oxo-2,6,10-pentadecatrienoic acid and n-dipropylamine
Elementary analysis: as $C_{24}H_{41}O_2N$.

|  | C | H | N |
|---|---|---|---|
| Calculated (%) | 76.75 | 11.00 | 3.73 |

| | C | H | N |
|---|---|---|---|
| Found (%) | 76.84 | 10.93 | 3.80 |

Mass (m/z): 375M+.

$^1$H-NMR (CDCl$_3$) δ: 0.87 (6H, t, J=4), 1.59 (6H, s), 1.80 (3H, s), 1.1–2.5 (14H), 2.12 (3H, s), 2.28 (2H, t, J=3), 3.1–3.3 (4H), 4.9–5.2 (2H), 5.3–5.5 (1H).

EXAMPLE 21

N-(2.6.10-trimethyl-14-oxo-2,6,10-pentadecatrienoyl)-diisopropylamine

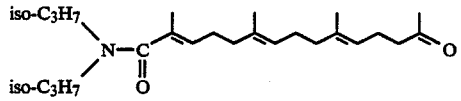

Starting materials: 2,6,10-trimethyl-14-oxo-2,6,10-pentadecatrienoic acid and diisopropylamine.

Elementary analysis: as C$_{24}$H$_{41}$O$_2$N.

| | C | H | N |
|---|---|---|---|
| Calculated (%) | 76.75 | 11.00 | 3.73 |
| Found (%) | 76.81 | 10.90 | 3.78 |

Mass (m/z): 375M+.

$^1$H-NMR (CDCl$_3$) δ: 1.29 (12H, d, J=4), 1.60 (6H, s), 1.81 (3H, s), 1.9–2.5 (10H), 2.12 (3H, s), 2.28 (2H, t, J=3), 3.5–3.8 (2H), 4.9–5.2 (2H), 5.2–5.4 (1H).

EXAMPLE 22

N-(2,6,10-trimethyl-14-oxo-2,6,10-pentadecatrienoyl-n-dibutylamine

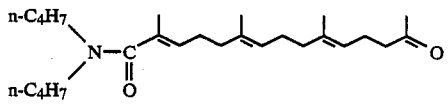

Starting materials: 2,6,10-trimethyl-14-oxo-2,6,10-pentadecatrienic acid and n-dibutylamine.

Elementary analysis: as C$_{26}$H$_{45}$O$_2$N.

| | C | H | N |
|---|---|---|---|
| Calculated (%) | 77.36 | 11.24 | 3.47 |
| Found (%) | 77.53 | 11.18 | 3.59 |

Mass (m/z): 403M+.

$^1$H-NMR (CDCl$_3$) δ: 0.87 (6H, t, J=4), 1.59 (6H, s), 1.80 (3H, s), 1.1–2.5 (18H), 2.12 (3H, s), 2.28 (2H, t, J=3), 3.1–3.3 (4H), 4.9–5.2 (2H), 5.3–5.5 (1H).

EXAMPLE 23

N-(2,6,10-trimethyl-14-oxo-2,6,10-pentadecatrienoyl)-diisobutylamine

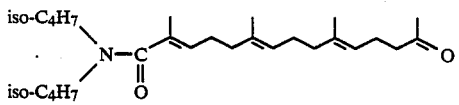

Starting materials: 2,6,10-trimethyl-14-oxo-2,6,10-pentadecatrienoic acid and diisobutylamine.

Elementary analysis: as C$_{26}$H$_{45}$O$_2$N.

| | C | H | N |
|---|---|---|---|
| Calculated (%) | 77.36 | 11.24 | 3.47 |
| Found (%) | 74.43 | 11.18 | 3.50 |

Mass (m/z): 403M+.

$^1$H-NMR (CDCl$_3$) δ: 0.84 (12H, d, J=4), 1.59 (6H, s), 1.80 (3H, s), 1.1–2.5 (14H), 2.11 (3H, s), 3.18 (4H, d, J=6), 4.9–5.2 (2H), 5.3–5.6 (1H).

EXAMPLE 24

2,6,10-trimethyl-14-oxo-2,6,10-pentadecatrienamide

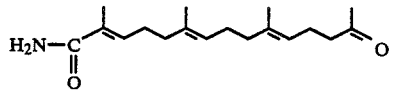

Starting materials: 2,6,10-trimethyl-14-oxo-2,6,10-pendadecatrienoic acid and ammonia water (28% ammonia water).

Elementary analysis: as C$_{18}$H$_{29}$O$_2$N.

| | C | H | N |
|---|---|---|---|
| Calculated (%) | 74.18 | 10.03 | 4.81 |
| Found (%) | 74.32 | 9.96 | 4.85 |

Mass (m/z): 291M+.

$^1$H-NMR (CDCl$_3$) δ: 1.60 (6H, s), 1.83 (3H, s), 1.9–2.5 (10H), 2.12 (3H, s), 2.33 (2H, t, J=3), 4.9–5.2 (2H), 5.5–5.8 (1H), 6.2–6.5 (2H).

EXAMPLE 25

2,6,10-trimethyl-14-oxo-2,6,10-pentadecatrienoyl)ethylamine

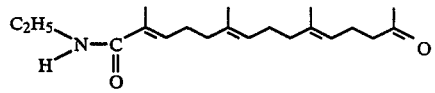

Starting materials: 2,6,10-trimethyl-14-oxo-2,6,10-pentadecatrienoic acid and ethylamine (70% aqueous ethylamine solution).

Elementary analysis: as C$_{20}$H$_{33}$O$_2$N.

| | C | H | N |
|---|---|---|---|
| Calculated (%) | 75.19 | 10.41 | 4.38 |
| Found (%) | 75.31 | 10.33 | 4.39 |

Mass (m/z): 319M+.

$^1$H-NMR (CDCl$_3$) δ: 1.15 (3H, t, J=4), 1.60 (6H, s), 1.82 (3H, s), 1.9–2.6 (10H), 2.12 (3H, s), 2.28 (2H, t, J=3), 3.1–3.5 (2H), 4.9–5.2 (2H), 5.5–5.8 (1H), 6.1–6.3 (1H).

EXAMPLE 26

2,6,10-trimethyl-14-oxo-2,6,10-pentadecatrienoyl)pyrrolidine

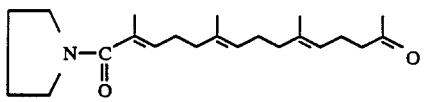

Starting materials: 2,6,10-trimethyl-14-oxo-2,6,10-pentadecatrienoic acid and pyrrolidine.
Elementary analysis: as $C_{22}H_{35}O_2N$.

|  | C | H | N |
|---|---|---|---|
| Calculated (%) | 76.47 | 10.21 | 4.05 |
| Found (%) | 76.64 | 10.08 | 4.13 |

Mass (m/z): 345M+.
$^1$H-NMR (CDCl$_3$) δ: 1.60 (6H, s), 1.82 (3H, s), 1.9–2.4 (14H), 2.11 (3H, s), 2.28 (2H, t, J=3), 3.3–3.6 (4H), 4.9–5.2 (2H), 5.5–5.7 (1H).

EXAMPLE 27

2,6,10-trimethyl-14-oxo-2,6,10-pentadecatrienoyl)-piperidine

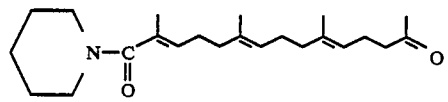

Starting materials: 2,6,10-trimethyl-14-oxo-2,6,10-pentadecatrienoic acid and piperidine.
Elementary analysis: as $C_{23}H_{37}O_2N$.

|  | C | H | N |
|---|---|---|---|
| Calculated (%) | 76.83 | 10.37 | 3.90 |
| Found (%) | 76.95 | 10.21 | 3.94 |

Mass (m/z): 359M+.
$^1$H-NMR (CDCl$_3$) δ: 1.59 (6H, s), 1.81 (3H, s), 1.9–2.5 (16H), 2.12 (3H, s), 2.28 (2H, t, J=3), 3.3–3.6 (4H), 4.9–5.2 (2H), 5.3–5.6 (1H).

EXAMPLE 28

2,6,10-trimethyl-14-oxo-2,6,10-pentadecatrienoyl)-3-pyrroline

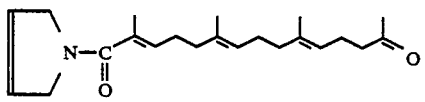

Starting materials: 2,6,10-trimethyl-14-oxo-2,6,10-pentadecatrienoic acid and 3-pyrroline.
Elementary analysis: as $C_{22}H_{33}O_2N$.

|  | C | H | N |
|---|---|---|---|
| Calculated (%) | 76.92 | 9.68 | 4.08 |
| Found (%) | 77.15 | 9.47 | 4.13 |

Mass (m/z): 343M+.
$^1$H-NMR (CDCl$_3$) δ: 1.60 (6H, s), 1.85 (3H, s), 1.9–2.6 (10H), 2.11 (3H, s), 2.28 (2H, t, J=3), 4.1–4.3 (4H), 4.9–5.2 (2H), 5.5–5.9 (2H), 6.28 (1H, t, J=1).

EXAMPLE 29

2,6,10-trimethyl-14-oxo-2,6,10-pentadecatrienoyl)imidazole

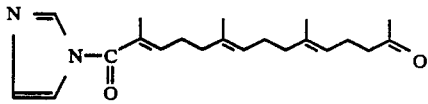

Starting materials: 2,6,10-trimethyl-14-oxo-2,6,10-pentadecatrienoic acid and imidazole (imidazole/pyridine solution).
Elementary analysis: as $C_{21}H_{30}O_2N_2$.

|  | C | H | N |
|---|---|---|---|
| Calculated (%) | 73.64 | 8.83 | 8.18 |
| Found (%) | 73.68 | 8.70 | 8.22 |

Mass (m/z): 342M+.
$^1$H-NMR (CDCl$_3$) δ: 1.59 (6H, s), 1.81 (3H, s), 2.12 (3H, s), 1.9–2.5 (12H), 4.9–5.2 (2H), 6.9–7.0 (1H), 7.0–7.1 (1H), 7.5–7.7 (1H), 8.29 (1H, s).

EXAMPLE 30

2,6,10-trimethyl-14-oxo-2,6,10-pentadecatrienoyl)morpholine

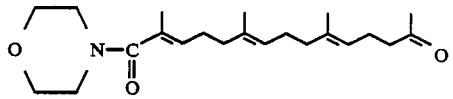

Starting materials: 2,6,10-trimethyl-14-oxo-2,6,10-pentadecatrienoic acid and morpholine
Elementary analysis: as $C_{22}H_{35}O_3N$.

|  | C | H | N |
|---|---|---|---|
| Calculated (%) | 73.09 | 9.76 | 3.87 |
| Found (%) | 73.13 | 9.75 | 3.93 |

Mass (m/z): 361M+.
$^1$H-NMR (CDCl$_3$) δ: 1.60 (6H, s), 1.81 (3H, s), 1.9–2.5 (12H), 2.12 (3H, s), 3.3–3.8 (8H), 4.9–5.2 (2H), 5.3–5.6 (1H).

EXAMPLE 31

N-(2,6,10-14-18-pentamethyl-22-oxo-2,6,10,14,18-tricosapentaenoyl)dimethylamine

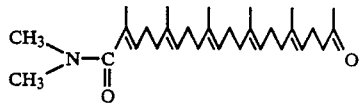

5 g of a starting material, i.e., 2,6,10,14,18-pentamethyl-22-oxo-2,6,10-14-18-tricosapentaenoic acid was dissolved in 30 ml of benzene. 2.8 g of thionyl chloride was added thereto and the mixture was heated under reflux for 30 minutes. The resulting solution was concentrated in vacuum and dissolved in 30 ml of benzene. The solution was added dropwise under cooling with ice to 10 ml of a 50% aqueous dimethylamine solution, and the mixture was agitated as such for 30 minutes.

The reaction solution was washed with dilute hydrochloric acid and then with water, and concentrated. The residue was purified by means of silica gel column chromatography to obtain 4.5 g (yield: 85%) of the title compound.

Elementary analysis: as $C_{30}H_{49}O_2N$.

|  | C | H | N |
|---|---|---|---|
| Calculated (%) | 79.07 | 10.48 | 3.07 |
| Found (%) | 79.20 | 10.77 | 3.18 |

Mass (m/z): 455M+.

$^1$N-NMR(CDCl$_3$) δ: 1.59 (12H, s), 1.81 (3H, s), 1.9–2.5 (18H), 2.12 (3H, s), 2.28 (2H, t, J=3), 2.95 (6H, s), 4.9–5.2 (4H), 5.4–5.6 (1H).

EXAMPLES 32 THROUGH 43

The following compounds were obtained in the same way as in Example 31. Although the starting materials used in Example 31 were 2,6,10,14,18-pentamethyl-22-oxo-2,6,10-14,18-tricosapentaenoic acid and dimethylamine, the desired compounds in the following examples were obtained by replacing these starting materials with the compounds described below.

EXAMPLE 32

N-(2,6,10,14,18-pentamethyl-22-oxo-2,6,10,14,18-tricosapentaenoyl)diethylamine

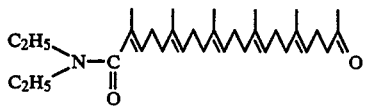

Starting materials: 2,6,10,14,18-pentamethyl-22-oxo-2,6,10,14,18-tricosapentaenoic acid and diethylamine Elementary analysis: as $C_{32}H_{53}O_2N$.

|  | C | H | N |
|---|---|---|---|
| Calculated (%) | 79.45 | 11.04 | 2.90 |
| Found (%) | 79.57 | 11.01 | 2.95 |

Mass (m/z): 483M+.

$^1$H-NMR (CDCl$_3$) δ: 1.11 (6H, t, J=4), 1.61 (12H, s), 1.80 (3H, s), 1.9–2.5 (18H), 2.12 (3H, s), 2.28 (2H, t, J=3), 3.33 (4H, q, J=4), 4.9–5.2 (4H), 5.3–5.5 (1H).

EXAMPLE 33

N-(2,6,10,14,18-pentamethyl-22-oxo-2,6,10,14,18-tricosapentaenoyl)-n-dipropylamine

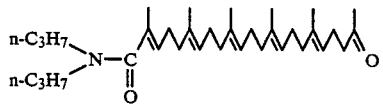

Starting materials: 2,6,10,14,18-pentamethyl-22-oxo-2,6,10,14,18-tricosapentaenoic acid and n-dipropylamine.

Elementary analysis: as $C_{34}H_{57}O_2N$.

|  | C | H | N |
|---|---|---|---|
| Calculated (%) | 79.79 | 11.23 | 2.74 |
| Found (%) | 79.95 | 11.01 | 2.81 |

Mass (m/z): 511M+.

$^1$H-NMR (CDCl$_3$) δ: 0.85 (6H, t, J=4), 1.59 (12H, s), 1.80 (3H, s), 1.1–2.5 (22H), 2.11 (3H, s), 2.28 (2H, t, J=3), 3.1–3.3 (4H), 4.9–5.2 (4H), 5.3–5.5 (1H).

EXAMPLE 34

N-(2,6,10,14,18-pentamethyl-22-oxo-2,6,10,14,18-tricosapentaenoyl)diisopropylamine

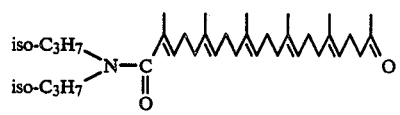

Starting materials: 2,6,10,14,18-pentamethyl-22-oxo-2,6,10,14,18-tricosapentaenoic acid and diisopropylamine.

Elementary analysis: as $C_{34}H_{57}O_2N$.

|  | C | H | N |
|---|---|---|---|
| Calculated (%) | 79.79 | 11.23 | 2.74 |
| Found (%) | 79.85 | 11.28 | 2.65 |

Mass (m/z): 511M+.

$^1$H-NMR (CDCl$_3$) δ: 1.30 (12H, d, J=4), 1.60 (12H, s), 1.81 (3H, s), 1.9–2.5 (18H), 2.12 (3H, s), 2.27 (2H, t, J=3), 3.5–3.8 (2H), 4.9–5.2 (4H), 5.2–5.4 (1H).

EXAMPLE 35

N-(2,6,10,14,18-pentamethyl-22-oxo-2,6,10,14,18-tricosapentaenoyl)-n-dibutylamine

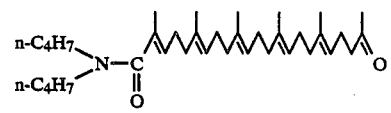

Starting materials: 2,6,10,14,18-pentamethyl-22-oxo-2,6,10,14,18-tricosapentaenoic acid and n-dibutylamine.

Elementary analysis: as $C_{36}H_{61}O_2N$.

|  | C | H | N |
|---|---|---|---|
| Calculated (%) | 80.09 | 11.39 | 2.59 |
| Found (%) | 80.19 | 11.42 | 2.65 |

Mass (m/z): 539M+.

$^1$H-NMR (CDCl$_3$) δ: 0.85 (6H, t, J=4), 1.60 (12H, s), 1.81 (3H, s), 1.1–2.5 (26H), 2.12 (3H, s), 2.28 (2H, t, J=3), 3.1–3.3 (4H), 4.9–5.2 (4H), 5.3–5.5 (1H).

EXAMPLE 36

N-(2,6,10,14,18-pentamethyl-22-oxo-2,6,10,14,18-tricosapentaenoyl)diisobutylamine

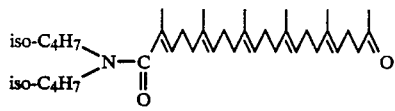

Starting materials: 2,6,10,14,18-pentamethyl-22-oxo-2,6,10,14,18-tricosapentaenoic acid and diisobutylamine.

Elementary analysis: as $C_{36}H_{61}O_2N$.

|  | C | H | N |
|---|---|---|---|
| Calculated (%) | 80.09 | 11.39 | 2.59 |
| Found (%) | 80.21 | 11.30 | 2.61 |

Mass (m/z): 539M+.

$^1$H-NMR (CDCl$_3$) δ: 0.85 (12H, d, J=4), 1.61 (12H, s), 1.80 (3H, s), 1.1–2.5 (22H), 2.11 (3H, s), 3.16 (4H, d, J=6), 4.9–5.2 (4H), 5.3–5.6 (1H).

EXAMPLE 37

N-(2,6,10,14,18-pentamethyl-22-oxo-2,6,10,14,18-tricosapentaenamide

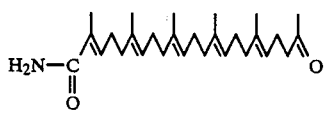

Starting materials: 2,6,10,14,18-pentamethyl-22-oxo-2,6,10,14,18-tricosapentaenoic acid and ammonia water (28% ammonia water).

Elementary analysis: as $C_{28}H_{45}O_2N$.

|  | C | H | N |
|---|---|---|---|
| Calculated (%) | 78.63 | 10.61 | 3.28 |
| Found (%) | 78.87 | 10.40 | 3.35 |

Mass (m/z): 427M+.

$^1$H-NMR (CDCl$_3$) δ: 1.59 (12H, S), 1.84 (3H, S), 1.9–2.5 (18H), 2.12 (3H, S), 2.31 (2H, t, J=3), 4.9–5.2 (4H), 5.5–5.8 (1H), 6.2–6.5 (2H).

EXAMPLE 38

N-(2,6,10,14,18-pentamethyl-22-oxo-2,6,10,14,18-tricosapentaenoyo)ethylamine

Starting materials: 2,6,10,14,18-pentamethyl-22-oxo-2,6,10,14,18-tricosapentaenoic acid and ethylamine (70% aqueous ethylamine solution).

Elementary analysis: as $C_{30}H_{49}O_2N$.

|  | C | H | N |
|---|---|---|---|
| Calculated (%) | 79.07 | 10.84 | 3.07 |
| Found (%) | 79.23 | 10.67 | 3.19 |

Mass (m/z): 455M+.

$^1$H-NMR (CDCl$_3$) δ: 1.15 (3H, t, J=4), 1.61 (12H, s), 1.82 (3H, s), 1.9–2.6 (18H), 2.11 (3H, s), 2.27 (2H, t, J=3), 3.1–3.5(2H), 4.9–5.2 (4H), 5.5–5.8 (1H), 6.1–6.3 (1H).

EXAMPLE 39

N-(2,6,10,14,18-pentamethyl-22-oxo-2,6,10,14,18-tricosapentaenoyl)pyrrolidine

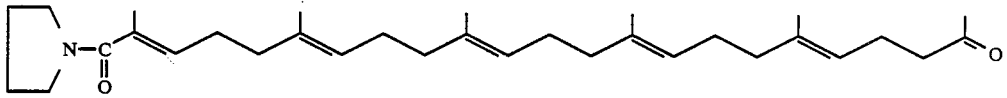

Starting materials: 2,6,10,14,18-pentamethyl-22-oxo-2,6,10,14,18-tricosapentaenoic acid and pyrrolidine.

Elementary analysis: as $C_{32}H_{51}O_2N$.

|  | C | H | N |
|---|---|---|---|
| Calculated (%) | 79.78 | 10.67 | 2.91 |
| Found (%) | 79.88 | 10.51 | 2.95 |

Mass (m/z): 481M+.

$^1$H-NMR (CDCl$_3$) δ: 1.60 (12H, s), 1.82 (3H, s), 1.9–2.4 (22H), 2.12 (3H, s), 2.28 (2H, t, J=3), 3.3–3.6 (4H), 4.9–5.2 (4H), 5.5–5.7(1H).

EXAMPLE 40

N-(2,6,10,14,18-pentamethyl-22-oxo-2,6,10,14,18-tricosapentaenoyl)piperidine

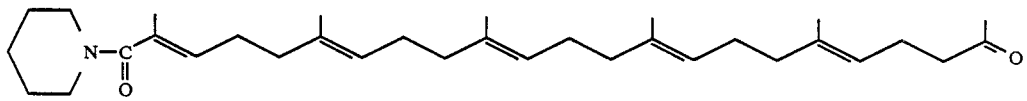

Starting materials: 2,6,10,14,18-pentamethyl-22-oxo-2,6,10,14,18-tricosapentaenoic acid and piperidine.

Elementary analysis: as $C_{33}H_{53}O_2N$.

|  | C | H | N |
|---|---|---|---|
| Calculated (%) | 79.94 | 10.78 | 2.83 |

| | C | H | N |
|---|---|---|---|
| Found (%) | 80.12 | 10.70 | 2.95 |

Mass (m/z): 495M+.

$^1$H-NMR (CDCl$_3$) δ: 1.59 (12H, s), 1.80 (3H, s), 1.9–2.5 (24H), 2.12 (3H, s), 2.28 (2H, t, J=3), 3.3–3.6 (4H), 4.9–5.2 (4H), 5.3–5.6 (1H).

EXAMPLE 41

N-(2,6,10,14,18-pentamethyl-22-oxo-2,6,10,14,18-tricosapentaenoyl)-3-pyrroline

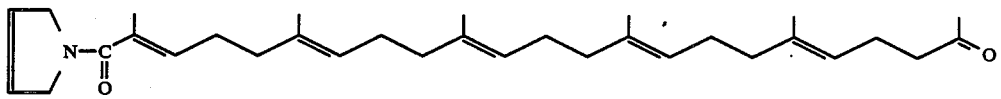

Starting materials: 2,6,10,14,18-pentamethyl-22-oxo-2,6,10,14,18-tricosapentaenoic acid and 3-pyrroline.
Elementary analysis: as C$_{32}$H$_{49}$O$_2$N.

| | C | H | N |
|---|---|---|---|
| Calculated (%) | 80.11 | 10.30 | 2.92 |
| Found (%) | 80.37 | 10.12 | 3.04 |

Mass (m/z): 479M+.

$^1$H-NMR (CDCl$_3$) δ: 1.60 (12H, s), 1.85 (3H, s), 1.9–2.6 (18H), 2.12 (3H, s), 2.28 (2H, t, J=3), 4.1–4.3 (4H), 4.9–5.2 (4H), 5.5–5.9 (2H), 6.30 (1H, t, J=1).

EXAMPLE 42

N-(2,6,10,14,18-pentamethyl-22-oxo-2,6,10,14,18-tricosapentaenoyl)imidazole

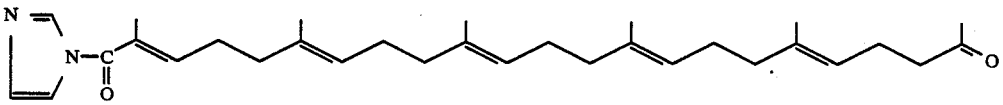

Starting materials: 2,6,10,14,18-pentamethyl-22-oxo-2,6,10,14,18-tricosapentaenoic acid and imidazole (imidazole/pyridine solution).
Elementary analysis: as C$_{31}$H$_{46}$O$_2$N.

| | C | H | N |
|---|---|---|---|
| Calculated (%) | 77.78 | 9.69 | 5.85 |
| Found (%) | 77.92 | 9.63 | 5.90 |

Mass (m/z): 478M+.

$^1$H-NMR (CDCl$_3$) δ: 1.59 (12H, s), 1.81 (3H, s), 2.12 (3H, s), 1.9–2.5 (20H), 4.9–5.2 (4H), 6.9–7.0 (1H), 7.0–7.1 (1H), 7.5–7.7 (1H), 8.29 (1H, s).

EXAMPLE 43

N-(2,6,10,14,18-pentamethyl-22-oxo-2,6,10,14,18-tricosapentaenoyl)morpholine

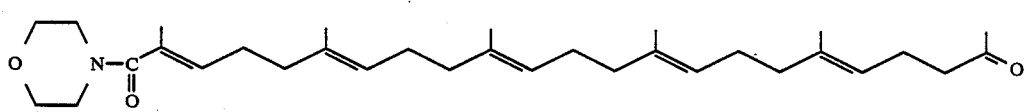

Starting materials: 2,6,10,14,18-pentamethyl-22-oxo-2,6,10,14,18-tricosapentaenoic acid and morpholine.
Elementary analysis: as C$_{32}$H$_{51}$O$_3$N.

| | C | H | N |
|---|---|---|---|
| Calculated (%) | 77.21 | 10.33 | 2.82 |
| Found (%) | 77.28 | 10.36 | 2.93 |

Mass (m/z): 497M+.

$^1$H-NMR (CDCl$_3$) δ: 1.60 (12H, s), 1.81 (3H, s), 1.9–2.5 (20H), 2.11 (3H, s), 3.3–3.8 (8H), 4.9–5.2 (4H), 5.3–5.6 (1H).

EXAMPLE 44

N-(2,6,10-trimethyl-14-oxo-2,6,10-pentadecatrienoyl)-diethanolamine

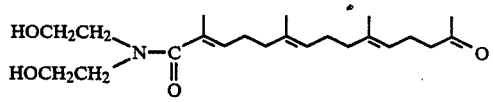

Starting materials: 2,6,10-trimethyl-14-oxo-2,6,10-pentadecatrienoic acid and diethanolamine.
Elementary analysis: as C$_{22}$H$_{37}$O$_4$N.

| | C | H | N |
|---|---|---|---|
| Calculated (%) | 69.62 | 9.83 | 3.69 |
| Found (%) | 69.51 | 9.78 | 3.73 |

Mass (m/z): 379M+.

$^1$H-NMR (CDCl$_3$) δ: 1.59 (6H, s), 1.81 (3H, s), 1.9–2.5 (10H), 2.11 (3H, s), 2.28 (2H, t, J=3), 3.2–3.8 (8H), 4.3–4.5 (2H), 4.9–5.2 (2H), 5.3–5.5 (1H)

EXAMPLE 45

N-(2,6,10-trimethyl-14-oxo-2,6,10-pentadecatrienoyl)-tert-butylethylamine

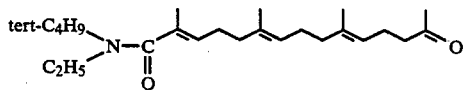

Starting material: 2,6,10-trimethyl-14-oxo-2,6,10-pentadecatrienoic acid and tert-butylethylamine.

Elementary analysis: as $C_{24}H_{41}O_2N$.

| | C | H | N |
|---|---|---|---|
| Calculated (%) | 76.75 | 11.00 | 3.73 |
| Found (%) | 76.88 | 10.84 | 3.65 |

Mass (m/z): 375M+.
$^1$H-NMR (CDCl$_3$) δ: 0.91 (9H, s), 1.11 (3H, t, J=4), 1.60 (6H, s), 1.82 (3H, s), 1.9–2.5 (10H), 2.11 (3H, s), 2.29 (2H, t, J=3), 3.35 (4H, q, J=4), 4.9–5.2 (2H), 5.4–5.6 (1H).

EXAMPLE 46

N-(2,6,10,14-tetramethyl-18-oxo-2,6,10,14-nonadecatetraenoyl)diethanolamine

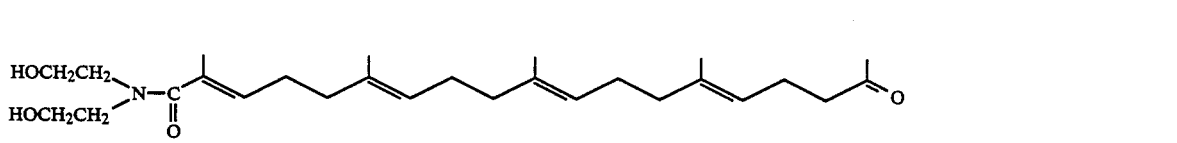

Starting materials: 2,6,10,14-tetramethyl-18-oxo-2,6,10,14-nonadecatetraenoic acid and diethanolamine
Elementary analysis: as $C_{27}H_{45}O_4N$.

| | C | H | N |
|---|---|---|---|
| Calculated (%) | 72.44 | 10.13 | 3.13 |
| Found (%) | 72.68 | 10.09 | 3.21 |

Mass (m/z): 447M+.
$^1$H-NMR (CDCl$_3$) δ: 1.59 (9H, s), 1.81 (3H, s), 1.9–2.5 (14H), 2.12 (3H, s), 2.28 (2H, t, J=3), 3.2–3.8 (8H), 4.3–4.5 (2H), 4.9–5.2 (3H), 5.4–5.6 (1H).

EXAMPLE 47

N-(2,6,10-tetramethyl-18-oxo-2,6,10,14-nonadecatetraenoyl)tert-butylethylamine

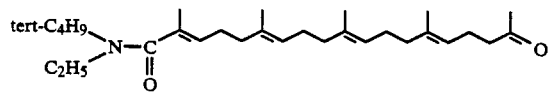

Starting materials: 2,6,10,14-tetramethyl-18-oxo-2,6,10,14-nonadecatetraenoic acid and tert-butylethylamine.
Elementary analysis: as $C_{29}H_{49}O_2N$.

| | C | H | N |
|---|---|---|---|
| Calculated (%) | 78.50 | 11.13 | 3.16 |

| | C | H | N |
|---|---|---|---|
| Found (%) | 78.67 | 11.11 | 3.21 |

Mass (m/z): 443M+.
$^1$H-NMR (CDCl$_3$) δ: 0.90 (9H, s), 1.12 (3H, t, J=4), 1.60 (9H, s), 1.81 (3H, s), 2.12 (3H, s), 1.9–2.5 (14H), 2.28 (2H, t, J=3), 3.34 (2H, q, J=4), 4.9–5.2 (3H), 5.3–5.5 (1H).

EXAMPLE 48

N-(2,6,10,14,18-pentamethyl-22-oxo-2,6,10,14,18-tricosapentaenoyl)diethanolamine

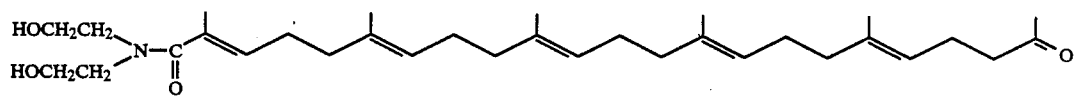

Starting materials: 2,6,10,14,18-pentamethyl-22-oxo-2,6,10,14,18-tricosapentaenoic acid and diethanolamine.

Elementary analysis: as $C_{32}H_{53}O_4N$

| | C | H | N |
|---|---|---|---|
| Calculated (%) | 74.52 | 10.36 | 2.72 |
| Found (%) | 74.75 | 10.18 | 2.66 |

Mass (m/z): 515 M+,
$^1$H-NMR (CDCl$_3$)δ: 1.61 (12H, s), 1.80 (3H, s), 1.9–2.5 (18H), 2.12 (3H, s), 2.28 (2H, t, J=3), 3.2–3.8 (8H), 4.3–4.5 (2H), 4.9–5.2 (4H), 5.3–5.5 (1H).

EXAMPLE 49

N-(2,6,10,14,18-pentamethyl-22-oxo-2,6,10,14,18-tricosapentaenoyl)-tert-butylamine

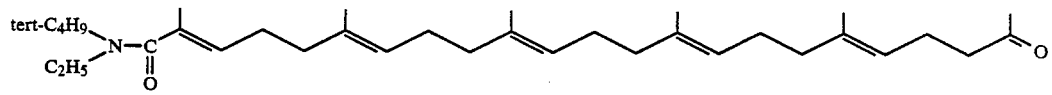

Starting materials: 2,6,10,14,18-pentamethyl-22-oxo-2,6,10,14,18-tricosapentaenoic acid and tert-butylethylamine.
Elementary analysis: as $C_{34}H_{57}O_2N$.

| | C | H | N |
|---|---|---|---|
| Calculated (%) | 79.79 | 11.23 | 2.74 |
| Found (%) | 79.95 | 11.12 | 2.85 |

Mass (m/z): 511 M+
$^1$H-NMR (CDCl$_3$)δ: 0.90 (9H, s), 1.11 (3H, t, J=4), 1.60 (12H, s), 1.81 (3H, s), 1.9–2.5 (18H), 2.12 (3H, s), 2.28 (2H, t, J=3), 3.35 (2H, q, J=4), 4.9–5.2 (4H), 5.4–5.6 (1H).

EXAMPLE 50

N-(2,6,10-trimethyl-14-oxo-2,6,10-pentadecatrienyl)acetamide

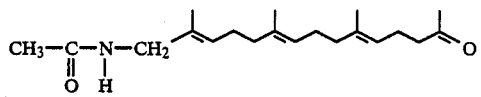

5 g of 2,6,10-trimethyl-14-oxo-2,6,10-pentadecatrienoic acid was dissolved in 30 ml of benzene. 4.1 g of thionyl chloride was added thereto and the mixture was heated under reflux for 30 minutes. The resulting solution was concentrated in vacuum and dissolved in 30 ml of benzene. The solution was added dropwise under cooling with ice to 30 ml of 28% ammonia water, and the resulting solution was agitated as such for 30 minutes. The reaction solution was washed with dilute hydrochloric acid and then with water, and concentrated. The residue was dissolved in 100 ml of benzene. 10.6 g of ethylene glycol and 0.3 g of p-toluenesulfonic acid were added thereto and the resulting mixture was heated under reflux for 5 hours by using an azeotropic dehydration tube. The reaction solution was washed with a sodium bicarbonate solution and then with water, and concentrated.

The residue was dissolved in 20 ml of tetrahydrofuran, to which was added dropwise 6 ml of a 70% solution of bis(2-methoxyethoxy)aluminum sodium hydride in toluene under cooling with ice and the mixture was agitated for 30 minutes. An aqueous caustic soda solution was added to the reaction solution, and the product was extracted with ether from the mixture, washed with water, and concentrated.

The residue was dissolved in ethanol. Dilute hydrochloric acid was added thereto and the mixture was allowed to stand at 50° C. for 2 hours and concentrated in vacuum. 5 ml of pyridine and 5 ml of acetic anhydride were added thereto, and the mixture was allowed to stand for 2 hours. The reaction solution was poured into dilute hydrochloric acid and extracted with benzene. The organic layer was washed with water and concentrated. The residue was purified by silica gel column chromatography to obtain 1.5 g (yield: 27%) of the title compound.

Elementary analysis: as $C_{20}H_{33}O_2N$.

|  | C | H | N |
|---|---|---|---|
| Calculated (%) | 75.19 | 10.41 | 4.38 |
| Found (%) | 75.37 | 10.25 | 4.44 |

Mass (m/z): 319 M+.

$^1$H-NMR (CDCl$_3$)δ: 1.60 (9H, s), 2.02 (3H, s), 1.9–2.5 (12H), 2.12 (3H, s), 2.7–2.9 (2H), 4.9–5.3 (3H), 6.1–7.1 (1H).

EXAMPLES 51 THROUGH 58

The following compounds were synthesized in the same way as described in Example 50. The compounds described in each example were used as the starting materials instead of the underlined compounds in Example 44, namely, 2,6,10-trimethyl-14-oxo-2,6,10-pentadecatrienoic acid, ammonia water, and acetic anhydride. (The order of the starting compound corresponds to the above order.)

EXAMPLE 51

N-(2,6,10-trimethyl-14-oxo-2,6,10-pentadecatrienyl)-propionamide

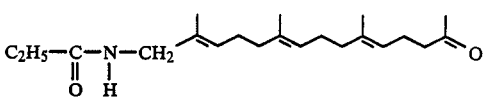

Starting materials: 2,6,10-trimethyl-14-oxo-2,6,10-pentadecatrienoic acid; ammonia water (28% ammonia water); and propionyl chloride.

Elementary analysis: as $C_{21}H_{35}O_2N$.

|  | C | H | N |
|---|---|---|---|
| Calculated (%) | 75.63 | 10.58 | 4.20 |
| Found (%) | 75.88 | 10.32 | 4.31 |

Mass (m/z): 333 M+.

$^1$H-NMR (CDCl$_3$)δ: 1.15 (3H, t, J=4), 1.60 (9H, s), 1.9–2.5 (2H), 2.12 (3H, s), 2.7–2.9 (2H), 3.1–3.6 (2H), 4.9–5.3 (3H), 6.1–7.1 (1H).

EXAMPLE 52

N-ethyl-N-(2,6,10-trimethyl-14-oxo-2,6,10-pentadecatrienyl)acetamide

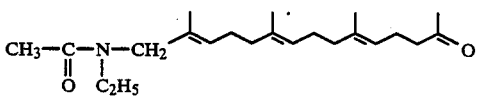

Starting materials: 2,6,10-trimethyl-14-oxo-2,6,10-pentadecatrienoic acid; ethylamine (70% aqueous ethylamine solution); and acetic anhydride.

Elementary analysis: as $C_{22}H_{37}O_2N$.

|  | C | H | N |
|---|---|---|---|
| Calculated (%) | 76.03 | 10.73 | 4.03 |
| Found (%) | 76.21 | 10.66 | 4.08 |

Mass (m/z): 347 M+.

$^1$H-NMR (CDCl$_3$)δ: 1.0–1.4 (3H), 1.59 (9H, s), 1.9–2.5 (12H), 2.01 (3H, s), 2.12 (3H, s), 2.6–2.7 (2H), 3.1–3.6 (2H), 4.9–5.3 (3H).

EXAMPLE 53

N-ethyl-N-(2,6,10-trimethyl-14-oxo-2,6,10-pentadecatrienyl)proionamide

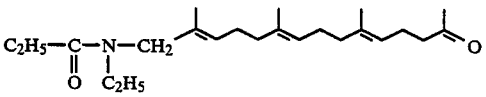

Starting materials: 2,6,10-trimethyl-14-oxo-2,6,10-pentadecatrienoic acid; ethylamine (70% aqueous ethylamine solution) and propionyl chloride.

Elementary analysis: as $C_{23}H_{39}O_2N$.

|  | C | H | N |
|---|---|---|---|
| Calculated (%) | 76.40 | 10.87 | 3.87 |

| | C | H | N |
|---|---|---|---|
| Found (%) | 76.58 | 10.66 | 3.95 |

Mass (m/z): 361 M+.
¹H-NMR (CDCl₃)δ: 1.0–1.4 (6H), 1.60 (9H, s),

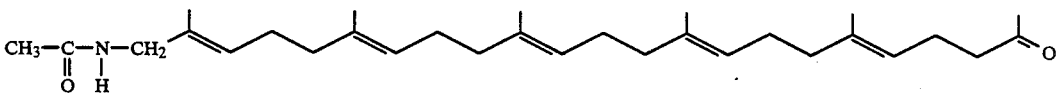

1.9–2.5 (12H), 2.12 (3H, s), 2.7–2.9 (2H), 3.1–3.6 (4H), 4.9–5.3 (3H).

EXAMPLE 54

N-(2,6,10,14,18-pentamethyl-22-oxo-2,6,10,14,18-tricosapentaenyl)acetamide

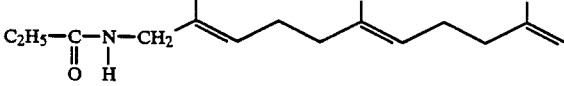

Starting materials: 2,6,10,14,18-pentamethyl-22-oxo-2,6,10,14,18-tricosapentaenoic acid; ammonia water (28% ammonia water); and acetic anhydride.
Elementary analysis: as C₃₀H₄₉O₂N.

| | C | H | N |
|---|---|---|---|
| Calculated (%) | 79.07 | 10.84 | 3.07 |
| Found (%) | 79.21 | 10.66 | 3.15 |

Mass (m/z): 455 M+.
¹H-NMR (CDCl₃)δ: 1.60 (15H, s), 2.01 (3H, s), 1.9–2.5 (20H), 2.12 (3H, s), 2.7–2.9 (2H), 4.9–5.3 (5H), 6.1–7.1 (1H).

EXAMPLE 55

N-(2,6,10,14,18-pentamethyl-22-oxo-2,6,10,14,18-tricosapentaenyl)propionamide

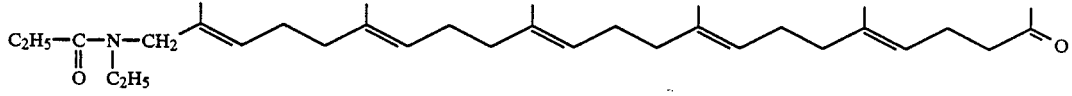

Starting materials: 2,6,10,14,18-pentamethyl-22-oxo-2,6,10,14,18-tricosapentaneonic acid; ammonia water (28% ammonia water); and propionyl chloride.
Elementary analysis: as C₃₁H₅₁O₂N.

| | C | H | N |
|---|---|---|---|
| Calculated (%) | 79.26 | 10.94 | 2.98 |
| Found (%) | 79.42 | 10.78 | 3.06 |

Mass (m/z): 469 M+.

¹H-NMR (CDCl₃)δ: 1.15 (3H, t, J=4), 1.59 (15H, s), 1.9–2.5 (20H), 2.12 (3H, s), 2.7–2.9 (2H), 3.1–3.6 (2H), 4.9–5.3 (5H), 6.1–7.1 (1H).

EXAMPLE 56

N-ethyl-N-(2,6,10,14,18-pentamethyl-22-oxo-2,6,10,14,18-tricosapentaenyl)acetamide Starting materials: 2,6,10,14,18-pentamethyl-22-oxo-2,6,10,14,18-tricosapentaenoic acid; ethylamine (70% aqueous ethylamine solution); and acetic anhydride.
Elementary analysis: as C₃₂H₅₃O₂N.

| | C | H | N |
|---|---|---|---|
| Calculated (%) | 79.45 | 11.04 | 2.90 |
| Found (%) | 79.58 | 10.98 | 2.97 |

Mass (m/z): 483 M+.
¹H-NMR (CDCl₃)δ: 1.0–1.4 (3H), 1.59 (15H, s), 1.9–2.5 (20H), 2.02 (3H, s), 2.12 (3H, s), 2.7–2.9 (2H), 3.1–3.6 (2H), 4.9–5.3 (5H).

EXAMPLE 57

N-ethyl-N-(2,6,10,14,18-pentamethyl-22-oxo-2,6,10,14,18-tricosapentaenyl)propionamide Starting materials: 2,6,10,14,18-pentamethyl-22-oxo-2,6,10,14,18-tricosapentaenoic acid; ethylamine (70% aqueous ethylamine solution); and propionyl chloride
Elementary analysis: as C₃₃H₅₅O₂N.

| | C | H | N |
|---|---|---|---|
| Calculated (%) | 79.62 | 11.14 | 2.81 |
| Found (%) | 79.78 | 11.11 | 2.97 |

Mass (m/z) 497 M+.
¹H-NMR (CDCl₃)δ: 1.0–1.4 (6H), 1.61 (15H, s), 2.11 (3H, s), 1.9–2.5 (20H), 2.7–2.9 (2H), 3.1–3.6 (4H), 4.9–5.3 (5H).

EXAMPLE 58

N-(11-ethoxycarbonyl-2,6,10-trimethyl-2,6,10-undecatrienoyl)dimethylamine

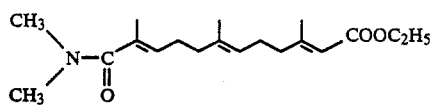

5 g of 11-ethoxycarbonyl-2,6,10-trimethyl-2,6,10-undecatrienoic acid was dissolved in 30 ml of benzene. 4.1 g of thinyl chloride was added thereto and the mixture was heated under reflux for 30 minutes. The resulting solution was concentrated in vacuum and dissolved in 30 ml of benzene. The solution was added dropwise under cooling with ice to 10 ml of a 50% aqueous dimethylamine solution, and the mixture was agitated as such for 30 minutes.

The reaction solution was washed with dilute hydrochloric acid and then with water, and concentrated. The residue was purified by means of silica gel chromatography to obtain 4.7 g (yield: 86%) of the title compound.

Elementary analysis: as $C_{19}H_{31}O_3N$.

|                | C     | H    | N    |
|----------------|-------|------|------|
| Calculated (%) | 70.99 | 9.72 | 4.36 |
| Found (%)      | 71.20 | 9.62 | 4.38 |

Mass (m/z): 321 M+.
$^1$H-NMR (CDCl$_3$)δ: 1.26 (3H, t, J=4), 1.60 (6H, s), 1.81 (3H, s), 1.9–2.3 (8H), 2.96 (6H, s), 4.14 (2H, q, J=4), 4.9–5.2 (1H), 5.3–5.5 (1H), 5.5–5.7 (1H).

EXAMPLES 59 THROUGH 75

The following compounds were synthesized in the same way as described in Example 58. The compounds described in each example were used as the starting materials instead of the underlined compounds in Example 52, namely, 11-ethoxycarbonyl-2,6,10-trimethyl-2,6,10-undecatrienoic acid and dimethylamine.

EXAMPLE 59

N-(11-ethoxycarbonyl-2,6,10-trimethyl-2,6,10-undecatrienoyl)diethylamine

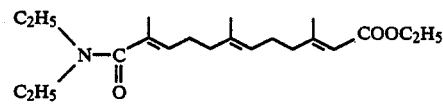

Starting materials: 11-ethoxycarbonyl-2,6,10-trimethyl-2,6,10-undecatrienoic acid and diethylamine.
Elementary analysis: as $C_{21}H_{35}O_3N$.

|                | C     | H     | N    |
|----------------|-------|-------|------|
| Calculated (%) | 72.16 | 10.09 | 4.01 |
| Found (%)      | 72.32 | 9.89  | 4.13 |

Mass (m/z): 349 M+.
$^1$H-NMR (CDCl$_3$)δ: 1.12 (6H, t, J=4), 1.26 (3H, t, J=4), 1.60 (6H, s), 1.80 (3H, s), 1.9–2.3 (8H), 3.34 (4H, q, J=4), 4.15 (2H, q, J=4), 4.9–5.2 (1H), 5.3–5.5 (1H), 5.5–5.7 (1H).

EXAMPLE 60

N-(11-ethoxycarbonyl-2,6,10-trimethyl-2,6,10-undecatrienoyl)n-dipropylamine

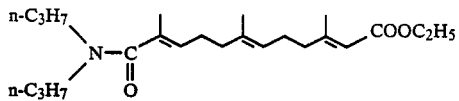

Starting materials: 11-ethoxycarbonyl-2,6,10-trimethyl-2,6,10-undecatrienoic acid and n-dipropylamine.
Elementary analysis: as $C_{23}H_{39}O_3N$.

|                | C     | H     | N    |
|----------------|-------|-------|------|
| Calculated (%) | 73.16 | 10.41 | 3.71 |
| Found (%)      | 73.28 | 10.39 | 3.78 |

Mass (m/z): 377 M+.
$^1$H-NMR (CDCl$_3$)δ: 0.87 (6H, t, J=4), 1.25 (3H, t, J=4), 1.1–2.3 (12H), 1.59 (6H, s), 1.81 (3H, s), 3.1–3.3 (4H), 4.15 (2H, q, J=4), 4.9–5.2 (1H), 5.3–5.5 (1H), 5.5–5.7 (1H).

EXAMPLE 61

N-(11-ethoxycarbonyl-2,6,10-trimethyl-2,6,10-undecatrienoyl)-diisopropylamine

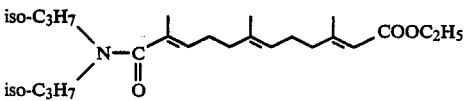

Starting materials: 11-ethoxycarbonyl-2,6,10-trimethyl-2,6,10-undecatrienoic acid and diisopropylamine.
Elementary analysis: as $C_{23}H_{39}O_3N$.

|                | C     | H     | N    |
|----------------|-------|-------|------|
| Calculated (%) | 73.16 | 10.41 | 3.71 |
| Found (%)      | 73.20 | 10.45 | 3.79 |

Mass (m/z): 377 M+.
$^1$H-NMR (CDCl$_3$)δ: 1.26 (3H, t, J=4), 1.31 (12H, d, J=4), 1.60 (6H, s), 1.80 (3H, s), 1.9–2.3 (8H), 3.5–3.8 (2H), 4.15 (2H, q, J=4), 4.9–5.2 (1H), 5.3–5.5 (1H), 5.5–5.7 (1H).

EXAMPLE 62

N-(11-ethoxycarbonyl-2,6,10-trimethyl-2,6,10-undecatrienoyl)pyrrolidine

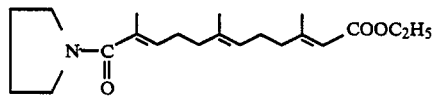

Starting materials: 11-ethoxycarbonyl-2,6,10-trimethyl-2,6,10-undecatrienoic acid and pyrrolidine.
Elementary analysis: as $C_{21}H_{33}O_3N$.

|                | C     | H    | N    |
|----------------|-------|------|------|
| Calculated (%) | 72.58 | 9.57 | 4.03 |

-continued

| | C | H | N |
|---|---|---|---|
| Found (%) | 72.65 | 9.60 | 4.01 |

Mass (m/z): 347 M+.
$^1$H-NMR (CDCl$_3$)δ: 1.26 (3H, t, J=4), 1.60 (6H, s), 1.81 (3H, s), 1.9–2.5 (12H), 3.3–3.6 (4H), 4.15 (2H, q, J=4), 4.9–5.2 (1H), 5.3–5.5 (1H), 5.5–5.7 (1H).

EXAMPLE 63

N-(11-ethoxycarbonyl-2,6,10-trimethyl-2,6,10-undecatrienoyl)piperidine

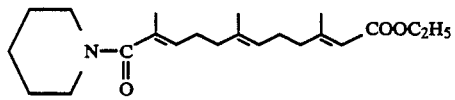

Starting materials: 11-ethoxycarbonyl-2,6,10-trimethyl-2,6,10-undecatrienoic acid and piperidine.
Elementary analysis: as $C_{22}H_{35}O_3N$.

| | C | H | N |
|---|---|---|---|
| Calculated (%) | 73.09 | 9.76 | 3.87 |
| Found (%) | 73.21 | 9.62 | 3.91 |

Mass (m/z): 361 M+.
$^1$H-NMR (CDCl$_3$)δ: 1.25 (3H, t, J=4), 1.60 (6H, s), 1.81 (3H, s), 1.9–2.5 (14H), 3.3–3.6 (4H), 4.15 (2H, q, J=4), 4.9–5.2 (1H), 5.3–5.5 (1H), 5.5–5.7 (1H).

EXAMPLE 64

N-(15-ethoxycarbonyl-2,6,10,14-tetramethyl-2,6,10,14-pentadecatetraenoyl)dimethylamine

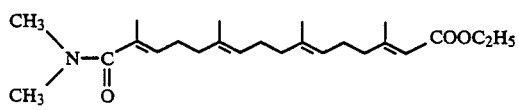

Starting materials: 15-ethoxycarbonyl-2,6,10,14-tetramethyl-2,6,10,14-pentadecatetraenoic acid and aqueous dimethylamine solution.
Elementary analysis: as $C_{24}H_{39}O_3N$.

| | C | H | N |
|---|---|---|---|
| Calculated (%) | 73.99 | 10.09 | 3.60 |
| Found (%) | 74.23 | 9.88 | 3.67 |

Mass (m/z): 389 M$^{30}$.
$^1$H-NMR (CDCl$_3$) δ: 1.25 (3H, t, J=4), 1.59 (9H, s), 1.80 (3H, s), 1.9–2.3 (12H), 2.95 (6H, s), 4.14 (2H, q, J=4), 4.9–5.2 (2H), 5.3–5.5 (1H), 5.5–5.7 (1H).

EXAMPLE 65

N-(1-ethoxycarbonyl-2,6,10,14-tetramethyl-2,6,10,14-pentadecatetraenoyl)diethylamine

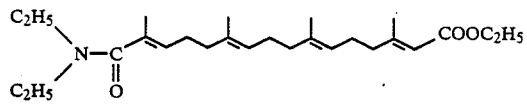

Starting materials: 15-ethoxycarbonyl-2,6,10,14-tetramethyl-2,6,10,14-pentadecatetraenoic acid and diethylamine.
Elementary analysis: as $C_{26}H_{43}O_3N$.

| | C | H | N |
|---|---|---|---|
| Calculated (%) | 74.77 | 10.38 | 3.35 |
| Found (%) | 74.85 | 10.31 | 3.40 |

Mass (m/z): 417 M+.
$^1$H-NMR (CDCl$_3$) δ: 1.11 (6H, t, J=4), 1.26 (3H, t, J=4), 1.59 (9H, s), 1.81 (3H, s), 1.9–2.3 (12H), 3.35 (4H, q, J=4), 4.14 (2H, q, J=4), 4.9–5.2 (2H), 5.3–5.5 (1H), 5.5–5.7 (1H).

EXAMPLE 66

N-(1-ethoxycarbonyl-2,6,10,14-tetramethyl-2,6,10,14-pentadecatetraenoyl)-n-dipropylamine

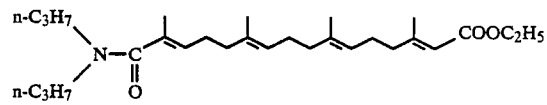

Starting materials: 15-ethoxycarbonyl-2,6,10,14-tetramethyl-2,6,10,14-pentadecatetraenoic acid and n-dipropylamine.
Elementary analysis: as $C_{28}H_{47}O_3N$.

| | C | H | N |
|---|---|---|---|
| Calculated (%) | 75.46 | 10.63 | 3.14 |
| Found (%) | 75.58 | 10.54 | 3.20 |

Mass (m/z): 445 M+.
$^1$H-NMR (CDCl$_3$) δ: 0.87 (6H, t, J=4), 1.26 (3H, t, J=4), 1.1–2.3 (16H), 1.60 (9H, s), 1.80 (3H, s), 3.1–3.3 (4H), 4.15 (2H, q, J=4), 4.9–5.2 (2H), 5.3–5.5 (1H), 5.5–5.7 (1H)

EXAMPLE 67

N-(1-ethoxycarbonyl-2,6,10,14-tetramethyl-2,6,10,14-pentadecatetraenoyl)-diisopropylamine

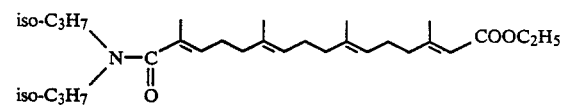

Starting materials: 15-ethoxycarbonyl-2,6,10,14-tetramethyl-2,6,10,14-pentadecatetraenoic acid and diisopropylamine.
Elementary analysis: as $C_{28}H_{47}O_3N$.

| | C | H | N |
|---|---|---|---|
| Calculated (%) | 75.46 | 10.63 | 3.14 |
| Found (%) | 75.62 | 10.47 | 3.22 |

Mass (m/z): 445 M+.
$^1$H-NMR (CDCl$_3$) δ: 1.26 (3H, t, J=4), 1.30 (12H, d, J=4), 1.60 (9H, s), 1.81 (3H, s), 1.9–2.3 (12H), 3.5–3.8 (2H), 4.14 (2H, q, J=4), 4.9–5.2 (2H), 5.3–5.5 (1H), 5.5–5.7 (1H).

EXAMPLE 68

N-(1-ethoxycarbonyl-2,6,10,14-tetramethyl-2,6,10,14-pentadecatetraenoyl)pyrrolidine

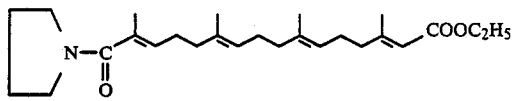

Starting materials: 15-ethoxycarbonyl-2,6,10,14-tetramethyl-2,6,10,14-pentadecatetraenoic acid and pyrrolidine.
Elementary analysis: as $C_{26}H_{41}O_3N$.

|  | C | H | N |
|---|---|---|---|
| Calculated (%) | 75.13 | 9.94 | 3.37 |
| Found (%) | 75.22 | 9.91 | 3.41 |

Mass (m/z): 415 M+.
$^1$H-NMR (CDCl$_3$) δ: 1.26 (3H, t, J=4), 1.59 (9H, s), 1.80 (3H, s), 1.9-2.5 (16H), 3.3—3.6 (4H), 4.14 (2H, q, J=4), 4.9-5.2 (2H), 5.3—5.5 (1H), 5.5-5.7 (1H).

EXAMPLE 69

N-(1-ethoxycarbonyl-2,6,10,14-tetramethyl-2,6,10,14-pentadecatetraenoyl)piperadine

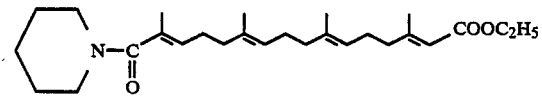

Starting materials: 15-ethoxycarbonyl-2,6,10,14-tetramethyl-2,6,10,14-pentadecatetraenoic acid and piperidine.
Elementary analysis: as $C_{27}H_{43}O_3N$.

|  | C | H | N |
|---|---|---|---|
| Calculated (%) | 75.48 | 10.09 | 3.26 |
| Found (%) | 75.56 | 10.02 | 3.37 |

Mass (m/z): 429 M+.
$^1$H-NMR (CDCl$_3$) δ: 1.25 (3H, t, J=4), 1.60 (9H, s), 1.80 (3H, s), 1.9-2.5 (18H), 3.3-3.6 (4H), 4.14 (2H, q, J=4), 4.9-5.2 (2H), 5.3-5.5 (1H), 5.5-5.7 (1H).

EXAMPLE 70

N-(19-ethoxycarbonyl-2,6,10,14,18-pentamethyl-2,6,10,14,18-nonadecapentaenoyl)dimethylamine

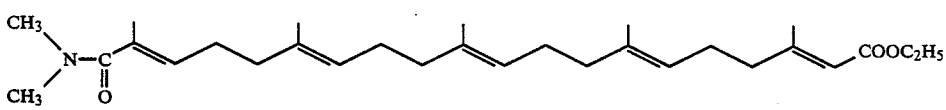

Starting materials: 19-ethoxycarbonyl-2,6,10,14,18-pentamethyl-2,6,10,14,18-nonadecapentaenoic acid and dimethylamine (50% aqueous dimethylamine solution)
Elementary analysis: as $C_{29}H_{47}O_3N$.

|  | C | H | N |
|---|---|---|---|
| Calculated (%) | 76.10 | 10.35 | 3.06 |
| Found (%) | 76.22 | 10.30 | 3.11 |

Mass (m/z): 457 M+.
$^1$H-NMR (CDCl$_3$) δ: 1.25 (3H, t, J=4), 1.60 (12H, s), 1.81 (3H, s), 1.9-2.3 (16H), 2.96 (6H, s), 4.15 (2H, q, J=4), 4.9-5.2 (3H), 5.3-5.5 (1H), 5.5-5.7 (1H).

EXAMPLE 71

N-(19-ethoxycarbonyl-2,6,10,14,18-pentamethyl-2,6,14,18-nonadecapentaenoyl)diethylamine

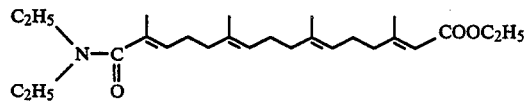

Starting materials: 19-ethoxycarbonyl-2,6,10,14,18-pentamethyl-2,6,10,14,18-nonadecapentaenoic acid and diethylamine.
Elementary analysis: as $C_{31}H_{51}O_3N$.

|  | C | H | N |
|---|---|---|---|
| Calculated (%) | 76.65 | 10.58 | 2.88 |
| Found (%) | 76.73 | 10.61 | 2.95 |

Mass (m/z): 485 M+.
$^1$H-NMR (CDCl$_3$) δ: 1.12 (6H, t, J=4), 1.25 (3H, t, J=4), 1.60 (12H, s), 1.81 (3H, s), 1.9-2.3 (16H), 3.35 (4H, q, J=4), 4.15 (2H, q, J=4), 4.9-5.2 (3H), 5.3-5.5 (1H), 5.5-5.7 (1H).

EXAMPLE 72

N-(19-ethoxycarbonyl-2,6,10,14,18-pentamethyl-2,6,10,14,18-nonadecapentaenoyl)-n-dipropylamine

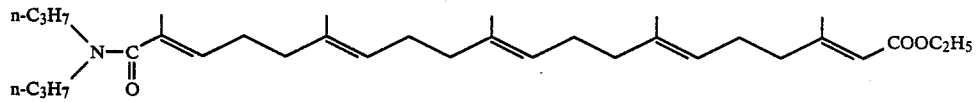

Starting materials: 19-ethoxycarbonyl-2,6,10,14,18-pentamethyl-2,6,10,14,18-nonadecapentaenoic acid and n-dipropylamine.
Elementary analysis: as $C_{33}H_{55}O_3N$.

|  | C | H | N |
|---|---|---|---|
| Calculated (%) | 77.14 | 10.79 | 2.73 |
| Found (%) | 77.25 | 10.83 | 2.69 |

Mass (m/z): 513 M+.

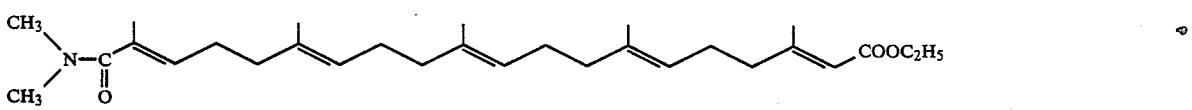

$^1$H-NMR (CDCl$_3$) δ: 0.88 (6H, t, J=4), 1.26 (3H, t, J=4), 1.1-2.3 (20H), 1.60 (12H, s), 1.81 (3H, s), 3.1-3.3 (4H), 4.15 (2H, q, J=4), 4.9-5.2 (3H), 5.3-5.5 (1H), 5.5-5.7 (1H).

EXAMPLE 73

N-(19-ethoxycarbonyl-2,6,10,14,18-pentamethyl-2,6,10,14,18-nonadecapentaenoyl-diisopropylamine Starting materials: 19-ethoxycarbonyl-2,6,10,14,18-pentamethyl-2,6,10,14,18-nonadecapentaenoic acid and diisopropylamine.

|  | C | H | N |
|---|---|---|---|
| Calculated (%) | 77.14 | 10.79 | 2.73 |
| Found (%) | 77.22 | 10.83 | 2.75 |

Mass (m/z): 513 M$^+$.
$^1$H-NMR (CDCl$_3$) δ: 1.26 (3H, t, J=4), 1.30 (12H, d, J=4), 1.61 (12H, s), 1.81 (3H, s), 1.9-2.3 (16H), 3.5-3.8 (2H), 4.15 (2H, q, J=4), 4.9-5.2 (3H), 5.3-5.5 (1H), 5.5-5.7 (1H).

EXAMPLE 74

N-(19-ethoxycarbonyl-2,6,10,14,18-pentamethyl-2,6,10,14,18-nonadecapentaenoyl)-pyrrolidine Starting materials: 19-ethoxycarbonyl-2,6,10,14,18-pentamethyl-2,6,10,14,18-nonadecapentaenoic acid and pyrrolidine.
Elementary analysis: as C$_{31}$H$_{49}$O$_3$N.

|  | C | H | N |
|---|---|---|---|
| Calculated (%) | 76.97 | 10.21 | 2.90 |
| Found (%) | 77.13 | 10.09 | 2.98 |

Mass (m/z): 483 M$^+$.
$^1$H-NMR (CDCl$_3$) δ: 1.26 (3H, t, J=4), 1.59. (12H, s), 1.80 (3H, s), 1.9-2.5 (20H), 3.3-3.6 (4H), 4.15 (2H, q, J=4), 4.9-5.2 (3H), 5.3-5.5 (1H), 5.5-5.7 (1H).

EXAMPLE 75

N-(19-ethoxycarbonyl-2,6,10,14,18-pentamethyl-2,6,10,14,18-nonadecapentaenoyl)piperadine Starting materials: 19-ethoxycarbonyl-2,6,10,14,18-pentamethyl-2,6,10,14,18-nonadecapentaenoic acid and piperidine.
Elementary analysis: as C$_{32}$H$_{51}$O$_3$N.

|  | C | H | N |
|---|---|---|---|
| Calculated (%) | 77.12 | 10.33 | 2.88 |
| Found (%) | 77.28 | 10.15 | 2.93 |

Mass (m/z): 497 M$^+$.
$^1$H-NMR (CDCl$_3$) δ: 1.26 (3H, t, J=4), 1.61 (12H, s), 1.80 (3H, s), 1.9-2.5 (22H), 3.3-3.6 (4H), 4.15 (2H, q, J=4), 4.9-5.2 (3H), 5.3-5.5 (1H), 5.5-5.7 (1H).

The following compound was obtained by the method as described in Example 1.

EXAMPLE 76

N-(2',6',10',14',-tetramethyl-18'-oxo-2',6',10',14'-nonadecatetraenoyl)-2-isopentenylamine Starting materials: 2,6,10,14-tetramethyl--18-oxo-2,6,10,14-nonadecatetraenoic acid and 2-isopentenylamine.
Elementary analysis: as C$_{28}$H$_{45}$O$_2$N.

|  | C | H | N |
|---|---|---|---|
| Calculated (%) | 78.63 | 10.61 | 3.28 |
| Found (%) | 78.84 | 10.55 | 3.34 |

Mass (m/z): 427 M$^+$.
$^1$H-NMR (CDCl$_3$) δ: 1.57 (6H, s), 1.60 (9H, s), 1.81 (3H, s), 1.9-2.5 (14H), 2.11 (3H, s), 2.28 (2H, t, J=3), 3.3-3.5 (2H), 4.9-5.3 (4H), 5.3-5.5 (1H), 6.2-6.4 (1H).

The embodiments of the invention in which an exclusive property or privilege is claimed are defined as follows:

1. A polyprenyl compound having the formula:

wherein X represents (1) a group of the formula:

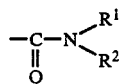

wherein R¹ and R², which can be the same or different, each represent hydrogen, lower alkyl, hydroxyalkyl, or lower alkenyl; atom; or (2) a group of the formula:

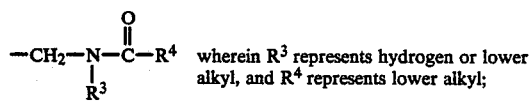 wherein R³ represents hydrogen or lower alkyl, and R⁴ represents lower alkyl;

Y represents a group of the formula: 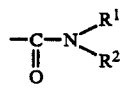

or a group of the formula:  wherein R⁵ represents hydrogen or lower alkyl, and n represents an integer of from 2 to 5.

2. A compound as defined in claim 1, wherein n is an integer of 4 or 5.

3. A compound as defined in claim 1, wherein X is

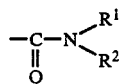

4. A compound as defined in claim 1, wherein Y is

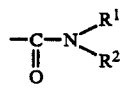

5. A compound as defined in claim 1, wherein Y is

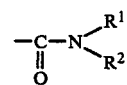

6. A compound as defined in claim 1, wherein X is

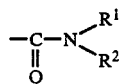

Y is

and n is an integer of 4 or 5.

7. A compound as defined in claim 1, wherein X is

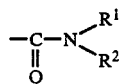

Y is

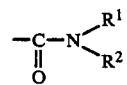

and n is an integer of 4 or 5.

8. A compound as defined in claim 1, wherein X is

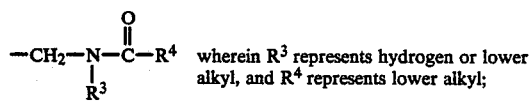

* * * * *